US011142470B2

(12) United States Patent
Robison et al.

(10) Patent No.: US 11,142,470 B2
(45) Date of Patent: Oct. 12, 2021

(54) DISINFECTION OF WATER MAINS USING ULTRAVIOLET LIGHT AND OXIDIZING AGENTS

(71) Applicant: AMERICAN WATER WORKS COMPANY, INC., Voorhees, NJ (US)

(72) Inventors: Martin L. Robison, O'Fallon, MO (US); Zia Bukhari, Voorhees, NJ (US); Yunjie Tu, Moorestown, NJ (US); Chandan Venkatesh, Cherry Hill, NJ (US)

(73) Assignee: American Water Works Company, Inc., Camden, NJ (US)

( * ) Notice: Subject to any disclaimer, the term of this patent is extended or adjusted under 35 U.S.C. 154(b) by 724 days.

(21) Appl. No.: 15/449,800

(22) Filed: Mar. 3, 2017

(65) Prior Publication Data

US 2017/0174536 A1  Jun. 22, 2017

Related U.S. Application Data

(63) Continuation-in-part of application No. 13/942,409, filed on Jul. 15, 2013, now Pat. No. 9,586,837.

(51) Int. Cl.
*C02F 1/32* (2006.01)
*C02F 1/72* (2006.01)
(Continued)

(52) U.S. Cl.
CPC ............ *C02F 1/325* (2013.01); *A61L 2/10* (2013.01); *A61L 2/183* (2013.01); *A61L 2/186* (2013.01);
(Continued)

(58) Field of Classification Search
CPC .. C02F 1/325; C02F 9/00; C02F 1/008; C02F 1/727; C02F 1/78; C02F 1/722; A61L 2/186; A61L 2/183; A61L 2/10
See application file for complete search history.

(56) References Cited

U.S. PATENT DOCUMENTS

| 2,017,042 A | 10/1935 | Dougherty |
| 2,461,517 A | 2/1949 | Carnevale |

(Continued)

FOREIGN PATENT DOCUMENTS

| DE | 102007038868 A1 | 2/2009 |
| WO | 2079095 A1 | 10/2002 |

OTHER PUBLICATIONS

International Search Report and Written Opinion dated May 2, 2018 in International Patent Application No. PCT/US2018/020685, 11 pages.

(Continued)

*Primary Examiner* — Regina M Yoo

(74) *Attorney, Agent, or Firm* — BakerHostetler

(57) ABSTRACT

Methods and systems are provided for disinfecting water mains using ultraviolet (UV) light and advanced oxidation processes. One or more UV light sources are provided and secured to a movable device that moves axially in a pipe. The frequency and intensity of the UV light is determined based on characteristics of the pipe, such as its material and size. The rate at which the movable device moves through the pipe is also determined so that the interior surface of the pipe is properly disinfected. The movable device is remotely caused to move through the pipe. An oxidant supply component having a dispensing portion dispenses an oxidizing agent into the pipe. A portion of the emitted UV light may convert the dispensed oxidizing agent into additional oxidizing agents that further disinfect the pipe.

10 Claims, 15 Drawing Sheets

(51) Int. Cl.
*C02F 1/78* (2006.01)
*C02F 1/00* (2006.01)
*C02F 9/00* (2006.01)
*A61L 2/18* (2006.01)
*A61L 2/10* (2006.01)

(52) U.S. Cl.
CPC .............. *C02F 1/008* (2013.01); *C02F 1/722* (2013.01); *C02F 1/727* (2013.01); *C02F 1/78* (2013.01); *C02F 9/00* (2013.01); *A61L 2202/11* (2013.01); *A61L 2202/14* (2013.01); *C02F 2201/008* (2013.01); *C02F 2201/009* (2013.01); *C02F 2201/326* (2013.01); *C02F 2201/3225* (2013.01); *C02F 2201/3227* (2013.01); *C02F 2209/008* (2013.01); *C02F 2303/04* (2013.01); *C02F 2305/023* (2013.01); *C02F 2307/14* (2013.01); *Y02A 20/212* (2018.01)

(56) References Cited

U.S. PATENT DOCUMENTS

| | | | |
|---|---|---|---|
| 2,887,118 A | 5/1959 | Loeffler et al. | |
| 3,074,098 A | 1/1963 | Downing | |
| 3,267,504 A * | 8/1966 | Cook | B08B 9/051 15/104.14 |
| 3,833,175 A | 9/1974 | Pulk et al. | |
| 4,073,302 A | 2/1978 | Jones | |
| 4,418,437 A | 12/1983 | French | |
| 4,763,376 A | 8/1988 | Spurlock et al. | |
| 5,020,188 A | 6/1991 | Walton | |
| 5,113,885 A | 5/1992 | Ramsey et al. | |
| 5,311,641 A | 5/1994 | Matsuura | |
| 5,317,782 A | 6/1994 | Matsuura et al. | |
| 5,322,080 A | 6/1994 | Rankin et al. | |
| 5,322,569 A | 6/1994 | Titus et al. | |
| 5,377,381 A | 1/1995 | Wilson et al. | |
| 5,528,789 A | 6/1996 | Rostamo | |
| 5,561,883 A | 10/1996 | Landry et al. | |
| 5,915,395 A | 6/1999 | Smith | |
| 6,206,016 B1 | 3/2001 | MacNeil et al. | |
| 6,371,631 B1 | 4/2002 | Reutemann | |
| 6,653,647 B1 | 11/2003 | Vilarasau Alegre | |
| 7,159,600 B2 | 1/2007 | MacNeil et al. | |
| 7,812,328 B2 | 10/2010 | Betz | |
| 8,308,137 B2 | 11/2012 | Alles | |
| 8,549,697 B1 | 10/2013 | Moyher, Jr. et al. | |
| 9,586,837 B2 | 3/2017 | Robison | |
| 2005/0022844 A1 * | 2/2005 | Field | A47L 11/283 134/6 |
| 2007/0210236 A1 | 9/2007 | Yungner et al. | |
| 2008/0302735 A1 | 12/2008 | Denkewicz, Jr. et al. | |
| 2011/0004342 A1 | 1/2011 | Knopow et al. | |
| 2012/0313014 A1 | 12/2012 | Stibich et al. | |
| 2012/0313532 A1 | 12/2012 | Stibich et al. | |
| 2012/0315186 A1 | 12/2012 | Davis | |
| 2013/0175460 A1 | 7/2013 | Farren | |
| 2017/0107128 A1 * | 4/2017 | Buschmann | A01N 37/16 |

OTHER PUBLICATIONS

Non-Final Office Action dated Mar. 24, 2016 in U.S. Appl. No. 13/942,409, 30 pages.
Final Office Action dated Oct. 13, 2015 in U.S. Appl. No. 13/942,409, 16 pages.
Non-Final Office Action dated May 20, 2015 in U.S. Appl. No. 13/942,409, 18 pages.

* cited by examiner

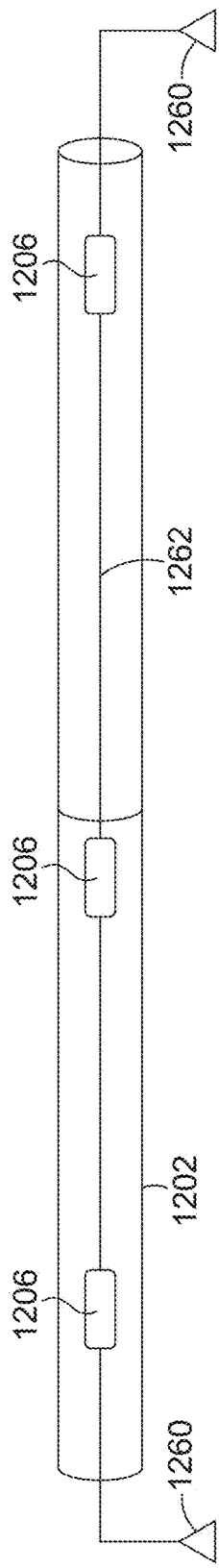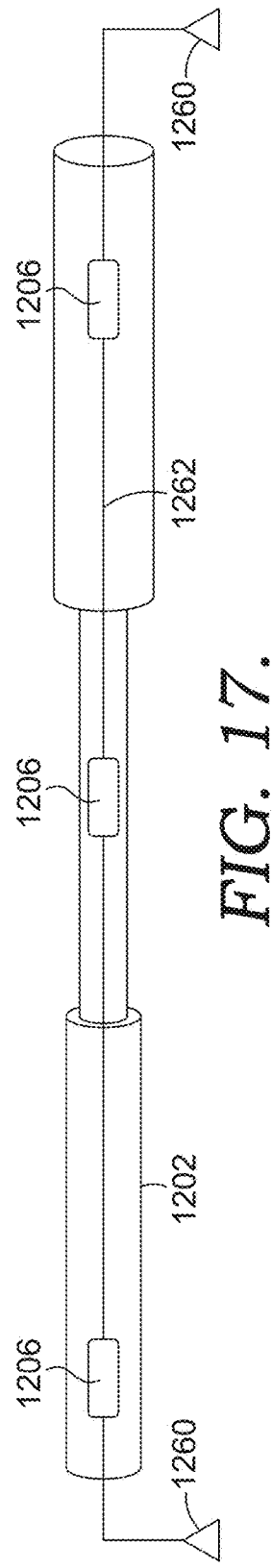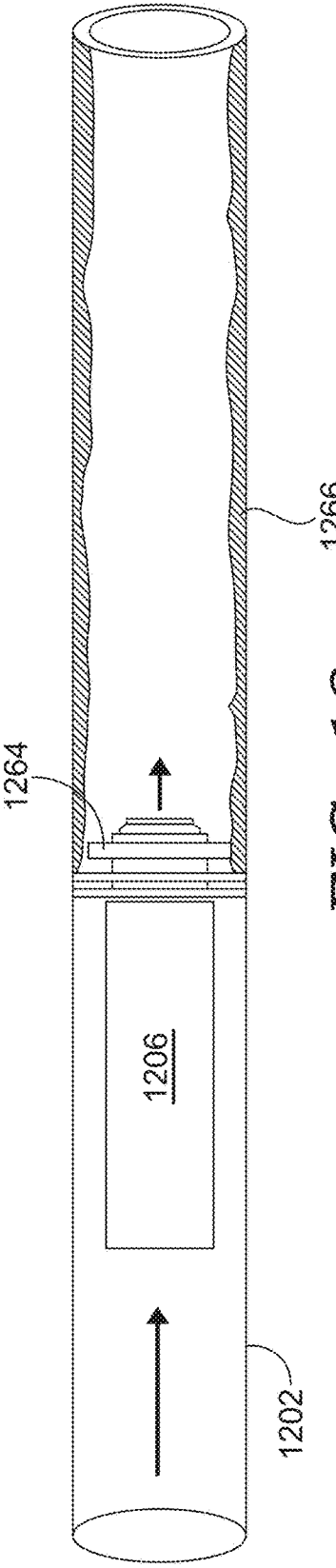

DISINFECTION OF WATER MAINS USING ULTRAVIOLET LIGHT AND OXIDIZING AGENTS

CROSS-REFERENCE TO RELATED APPLICATIONS

This application is a continuation-in-part of and claims priority to U.S. application Ser. No. 13/942,409, filed Jul. 15, 2013, entitled "Disinfection of Water Mains Using Ultraviolet Light." The entirety of the aforementioned application is incorporated by reference herein.

BACKGROUND

When a new water main is installed, it is disinfected prior to being used to transport water. The typical disinfection method is super-chlorination of approximately 50 parts-per-million (ppm) of free chlorine. The chlorinated water may sit in the water main for prolonged periods of time, sometimes up to 24 hours. The main is then flushed with system water. This process requires a trailer stocked with pressure pumps, barrels to hold bleach, metering pumps, pressure gauges, generators to power the pumps, and a variety of piping. All of this equipment requires significant capital expenditure and is also prone to maintenance, which can be costly and time consuming.

SUMMARY

Embodiments of the invention are defined by the claims below, not this summary. A high-level overview of various aspects of the invention are provided here for that reason, to provide an overview of the disclosure, and to introduce a selection of concepts that are further described in the detailed description section below. This summary is not intended to identify key features or essential features of the claimed subject matter, nor is it intended to be used as an aid in isolation to determine the scope of the claimed subject matter. In brief and at a high level, this disclosure describes, among other things, methods, systems and apparatuses for using ultraviolet (UV) light to disinfect a pipe, such as a water main, prior to placing the pipe in service. A UV light source may be coupled to a remotely controlled device that moves axially in the pipe to provide the proper dosage of the UV light to the interior surface of the pipe. The intensity and frequency needed from the UV light is determined based on one or more characteristics of the pipe. The frequency range of the UV light, based on its purpose of disinfection, may be between 10 nm and 400 nm, and more specifically, between 100 nm and 280 nm, which is a short wave that may be used as a germicide. In some embodiments, one light source (e.g., one UV light) is utilized for a pipe, but in other embodiments, multiple UV lights are used to move the light source closer to the interior walls of the pipe. Further, the remotely controlled device may move axially in the pipe at a rate determined by the dosage needed to disinfect the interior surfaces of the pipe. The remotely controlled device may be connected to a winch that controls the movement of the device by way of a tether, such as a cable. Alternatively motorized mechanisms may be used.

In other embodiments, an oxidant supply component configured to emit oxidizing agents into the pipe may be provided. The oxidant supply component may be coupled to the remotely controlled device, such as in front of the UV light source. The emitted oxidizing agents may comprise oxygen ($O_2$), ozone ($O_3$), hydrogen peroxide ($H_2O_2$) or any other oxidizing agent. The emitted oxidizing agents may help to further disinfect the pipe by destroying contacted microorganisms, chemicals or other pollutants (collectively referred to herein as "contaminants"). In further embodiments, the UV light may interact with the oxidizing agents to generate additional oxidizing agents that may help to further disinfect the pipe by oxidizing contacted contaminants. For example, the UV light, in one embodiment, may come into contact with hydrogen peroxide such that free radicals or ozone is generated. In still other embodiments, the UV light may interact with the oxidizing agents to generate hydroxyl radicals (·OH) that may help to oxidize contaminants suspended within the pipe.

BRIEF DESCRIPTION OF THE SEVERAL VIEWS OF THE DRAWINGS

Illustrative embodiments of the present invention are described in detail below with reference to the attached drawing figures, and wherein:

FIG. 16 is a side elevation view of a system of sequentially tethered remotely controlled devices in accordance with an embodiment of the present invention;

FIG. 17 is a side elevation view of a system of sequentially tethered remotely controlled devices in accordance with an embodiment of the present invention;

FIG. 18 is a side elevation view of a pigging component coupled to a remotely controlled device in accordance with an embodiment of the present invention.

DETAILED DESCRIPTION

Figure 1:
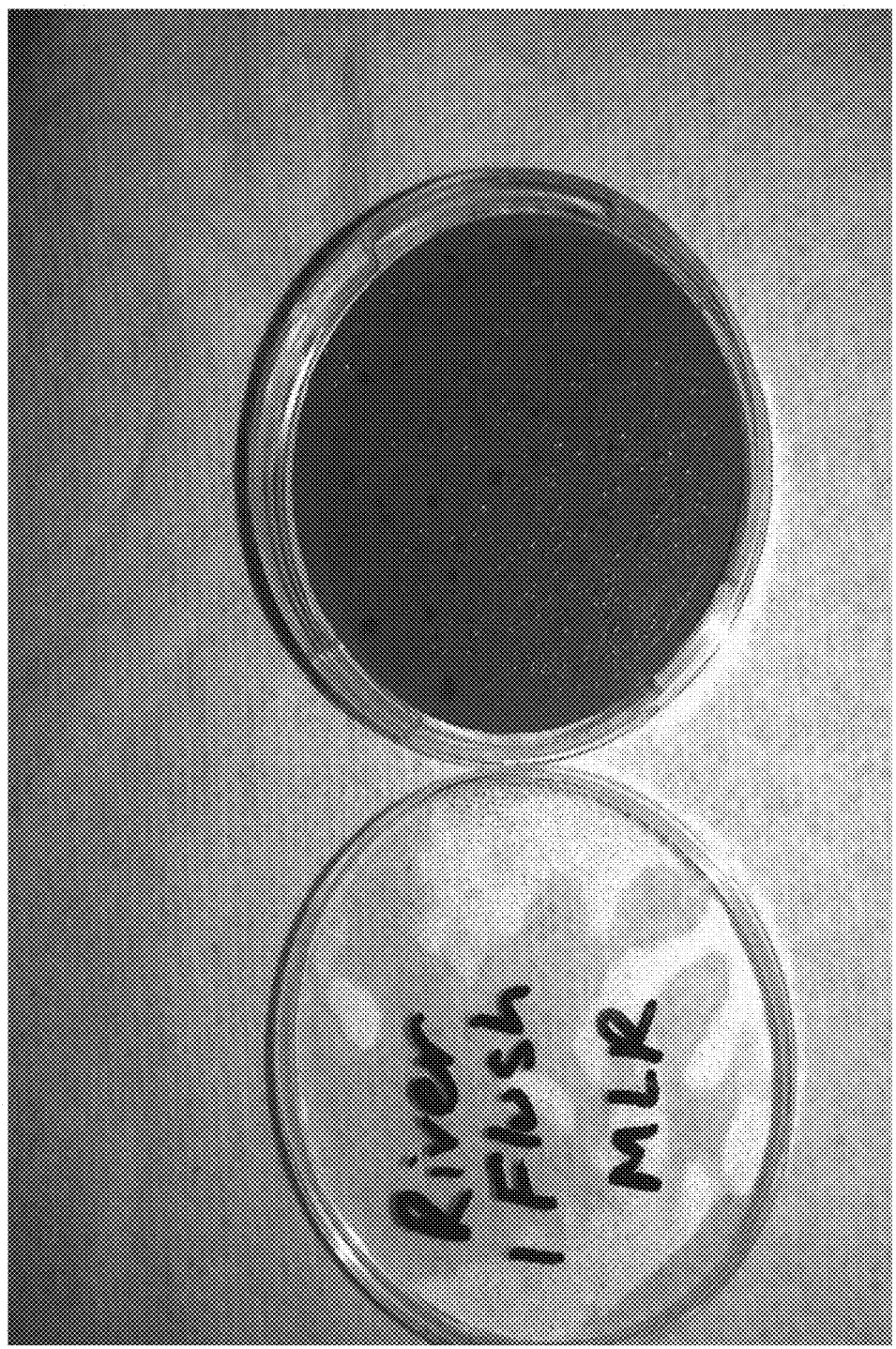
FIGS. 1 and 2 illustrate a petri dish with a sample of contaminated water taken from a pipe that was filled with Missouri River water then flushed once with tap water.

The subject matter of embodiments of the present invention is described with specificity herein to meet statutory requirements. But the description itself is not intended to necessarily limit the scope of claims. Rather, the claimed subject matter might be embodied in other ways to include different steps or combinations of steps similar to the ones described in this document, in conjunction with other present or future technologies. Terms should not be interpreted as implying any particular order among or between various steps herein disclosed unless and except when the order of individual steps is explicitly described.

In a first aspect of the present invention, a method is provided for disinfecting water mains using ultraviolet (UV) light. The method includes providing one or more UV light sources that are secured to a movable device that is sized to move axially inside of a pipe. A frequency and an intensity of the UV light from the one or more UV light sources is selected based at least on a material and a size of the pipe, and the pipe is to be disinfected prior to transporting a substance from one location to another location. Further, the method includes remotely causing the movable device to move axially inside of the pipe at a rate that is determined based on one or more characteristics of the pipe. The frequency and the intensity of the UV light and the rate of the movable device through the pipe indicate a dosage of the UV light in relation to the pipe.

In a second aspect of the present invention, a remotely controlled device is provided for transporting a UV light source through a water main for disinfection of the water main. The remotely controlled device includes a body portion that is mechanically coupled to the UV light source so that the UV light source remains centered within the water main as the remotely controlled device moves axially through the water main, the UV light source outputting omni-directional light such that as the remotely controlled device moves axially through the water main, interior surfaces of the water main are contacted by the UV light, the UV light disinfecting the interior surfaces of the water main as it moves through the water main at a rate determined by one or more characteristics of the water main. A frequency and an intensity of the UV light are selected based at least on a material and a size of the water main. Further, the remotely controlled device includes a plurality of movement mechanisms that are coupled to the body portion and that have contact with the interior surface of the water main and allow the remotely controlled device to move axially through the water main.

In a third aspect of the present invention, a remotely controlled UV disinfection system is provided that is used to disinfect water mains. The system includes a UV light source for disinfecting interior surfaces of the water mains and whose frequency and intensity are selected based at least on a material and a size of the water main. The system also includes a remotely controlled device for transporting the UV light source axially through a water main, the remotely controlled device moving axially through the water main at a rate determined based on the frequency and the intensity of the selected UV light source and on one or more characteristics of the water main. The remotely controlled device includes a body portion that is mechanically coupled to the UV light source, and movement mechanisms that are coupled to the body portion for moving the remotely controlled device axially through the water main.

In a fourth aspect of the present invention, a water-main disinfecting system is provided. The system includes a remotely-controlled carriage having a receiver. The receiver may be configured to receive instructions from a remote controller. The remote controller may be configured to send signals to the receiver and cause the carriage to move axially inside of a pipe. The system further includes a UV light source coupled to the remotely-controlled carriage and configured to emit UV light. The emitted UV light may irradiate a plurality of contaminants located on an interior surface of the pipe and/or suspended within the pipe. The system further includes an oxidant supply component configured to emit oxidizing agents into the pipe. The emitted oxidizing agents may oxidize the plurality of contaminants located on the interior surface of the pipe and/or suspended within the pipe.

The UV light source may emit UV light having wavelengths less between 100 and 300 nanometers. The oxidant supply component may include a storage component configured to store the oxidizing agents and a dispensing component configured to emit oxidizing agents. The dispensing component may be in communication with the storage component. The dispensing component may be configured to move axially inside the pipe. In some aspects, the dispensing component is coupled to the remotely-controlled carriage. In other aspects, the dispensing component moves axially inside the pipe independently of the remotely-controlled carriage. The remotely controlled carriage may have a forward end opposite a rearward end. The dispensing component may be coupled to the remotely-controlled carriage nearer to the forward end than is the UV light source such that the oxidizing agents are emitted in the pipe forward of the UV light source. The storage component may be maintained outside of the pipe. The oxidant supply component may further include an oxidizing agent generator configured to produce the oxidizing agents. The oxidizing agent generator may be in communication with the storage component. The emitted UV light may interact with at least a portion of the oxidizing agents to generate additional oxidizing agents. The additional oxidizing agents may oxidize the plurality of contaminants located on the interior surface of the pipe and/or suspended within the pipe. The oxidizing agents may include one or more of oxygen ($O_2$), ozone ($O_3$) and/or hydrogen peroxide ($H_2O_2$). The emitted UV light may interact with the oxidizing agents to generate hydroxyl radicals ($\cdot OH$). The hydroxyl radicals ($\cdot OH$) may oxidize contaminants suspended within the pipe.

The remotely-controlled carriage may include a body portion, a plurality of pairs of legs and a plurality of contact members. Each of the legs may have a first end opposite a second end. Each of the legs may be coupled proximate the first end to the body portion and may extend towards the interior surface of the pipe. Each of the plurality of contact members may be respectively coupled proximate the second ends of a respective pair of the plurality of pairs of legs. Each contact member of the plurality of contact members may be configured to contact the interior surface of the pipe. Each of the pairs of legs may be pinned together intermediate the first and second ends. In some aspects, each of the plurality of contact members may include a first contact member and a second contact member. Each said first contact member may be coupled to the second end of one of the pairs of legs and each said second contact member may be coupled to the second end of the other of the pairs of legs.

In a fifth aspect of the present invention, a method of disinfecting a pipe using an advanced oxidation process is provided. The method includes the step of providing a movable device that is sized to move axially inside of the pipe. The movable device may have one or more UV light sources coupled to the movable device between a forward end and a rearward end of the movable device. The method further includes the step of providing a supply of oxidizing agents. The supply of oxidizing agents may have a dispensing portion coupled to the movable device between the forward end and a forwardmost UV light source of the one or more UV light sources. The method further includes the step of treating an interior surface of the pipe and the fluid within the pipe by emitting an oxidizing agent from the dispensing portion into the fluid contained in the pipe and by emitting UV light from the one or more UV light sources. The method further includes the step of causing the movable device to move axially inside of the pipe at a rate that is determined based on one or more characteristics of the pipe and fluid contained in the pipe.

The method may also include the step of causing the movable device to move radially inside of the pipe. In some aspects, the method further includes the step of generating additional oxidizing agents by irradiating treated fluid with UV light emitted from the one or more UV light sources. The additional oxidizing agents may oxidize a plurality of contaminants located on the interior surface of the pipe and suspended within the pipe. In some aspects, the UV light emitted from the one or more UV light sources may have a wavelength between 100 nanometers and 400 nanometers. In other aspects, the UV light emitted from the one or more UV light sources may have a wavelength between 100 nanometers and 300 nanometers. The method may further include the step of generating hydroxyl radicals (·OH) by irradiating the treated fluid with UV light from the one or more UV light sources. The movable device may be caused to move axially through the pipe with a wireless controller.

In a sixth aspect of the present invention, a method of disinfecting a pipe using an advanced oxidation process is provided. The method includes the step of providing a movable device that is sized to move axially inside of the pipe. The movable device may have one or more UV light sources coupled to the movable device between a forward end and a rearward end of the movable device. The method further includes the step of providing a supply of hydrogen peroxide ($H_2O_2$). The supply of hydrogen peroxide may be in communication with a dispensing portion coupled to the movable device between the forward end and a forwardmost UV light source of the one or more UV light sources. The method further includes the step of emitting hydrogen peroxide into the pipe. The method further includes the step of converting a portion of the hydrogen peroxide into ozone ($O_3$) with UV light emitted from the one or more UV light sources. The method further includes the step of causing the movable device to move axially inside of the pipe at a rate that is determined based on one or more characteristics of the pipe and fluid contained in the pipe.

Figure 2:
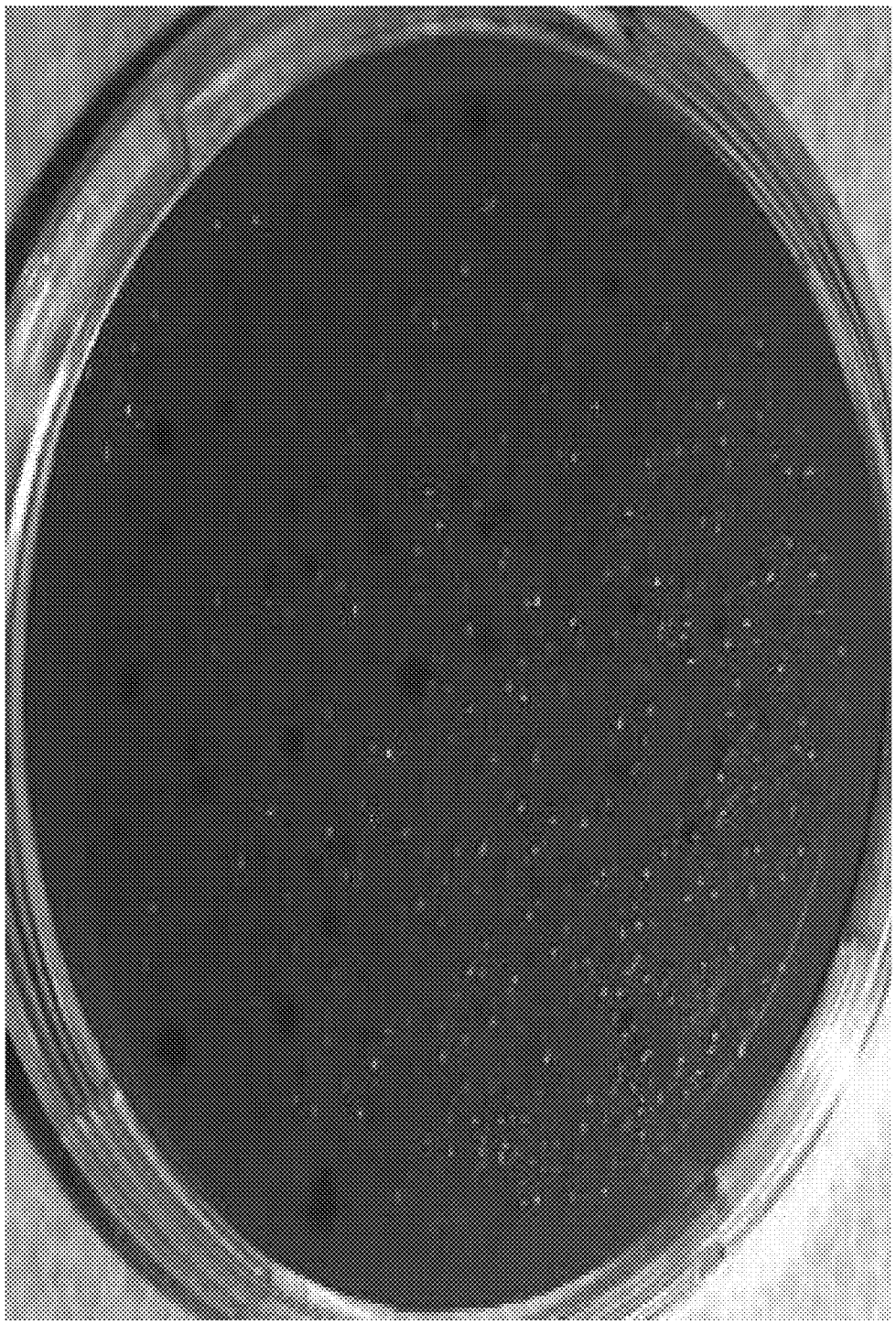

Referring to the drawings in general and initially to FIGS. 1 and 2, a petri dish is shown with a sample of contaminated water taken from a pipe that was filled with Missouri River water then flushed once with tap water. Multiple tests have been done to compare different methods of disinfection on the inside of a pipe, such as a water main. Preliminary tests were conducted to validate the sample and analysis method as well as to verify contamination levels prior to performing the disinfection procedures. These tests confirmed that the contamination procedure was successful and yielded the presence of appropriate coliform and non-coliform bacteria. Additionally, this method of main disinfection was tested with results showing effective and complete inactivation of pathogenic organisms. Here, a PVC pipe was filled with Missouri River water, and subsequently flushed once with tap water. The result of what is shown in FIGS. 1 and 2 is that the contamination was too numerous to count (TNTC). While there was no apparent total coliform growth, TNTC petri dishes are considered to potentially contain coliform bacteria, as the prolific growth of non-coliform bacteria can mask coliform growth.

Figure 3:
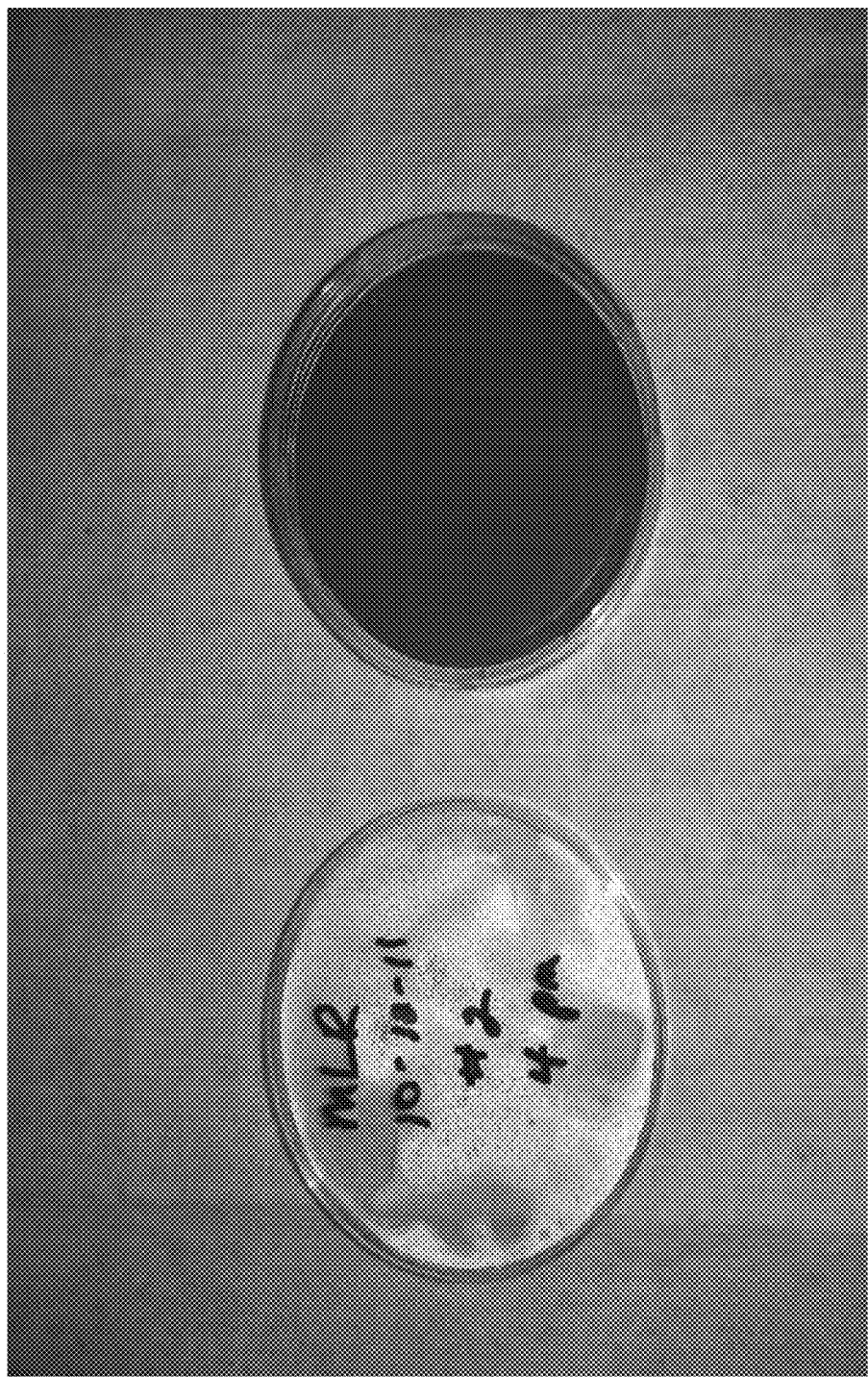
FIG. 3 illustrates a petri dish with a water sample taken after a process of super-chlorination has been applied to a pipe.

Initially, to compare disinfection using UV light with another form of disinfection, super-chlorination was used to disinfect the pipe. As shown in FIG. 3, a petri dish has a water sample taken after a process of super-chlorination has been applied to a pipe. Super-chlorination is a method that has been used to disinfect new water mains. The method of super-chlorination may include pumping bleach into the main to attain greater than 50 ppm of chlorine. The solution sits in the pipe for a minimum of 24 hours. After this waiting period, the super-chlorinated water is flushed out while a de-chlorinating agent is added to neutralize the highly chlorinated water. This method is not only costly, but dangerous for those involved. The results, as expected, show zero Colony Forming Units (CFU), or zero coliform bacteria.

Figure 4:
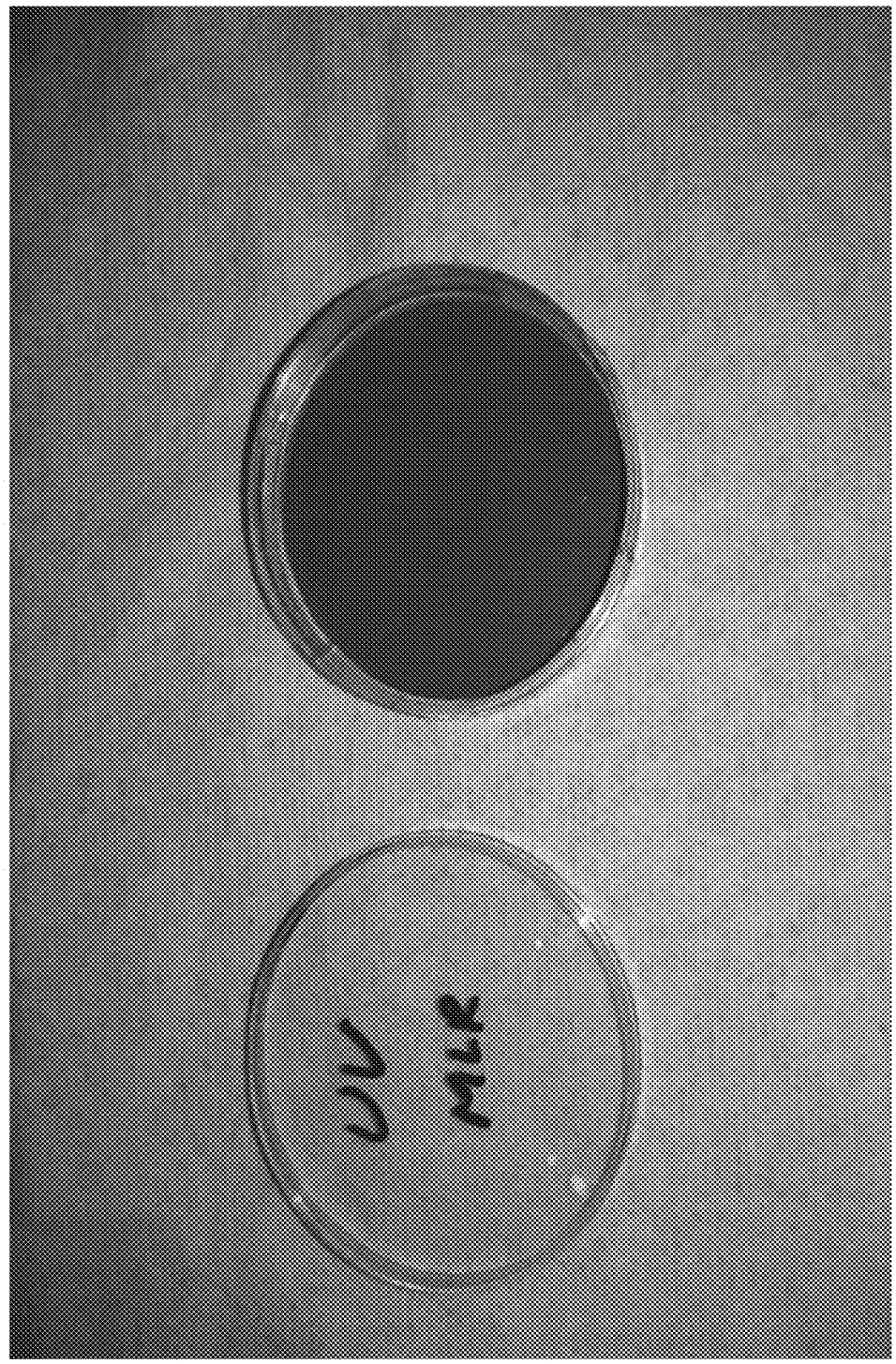
FIG. 4 illustrates a petri dish with a water sample taken after UV light has been applied to a pipe.
Figure 5:
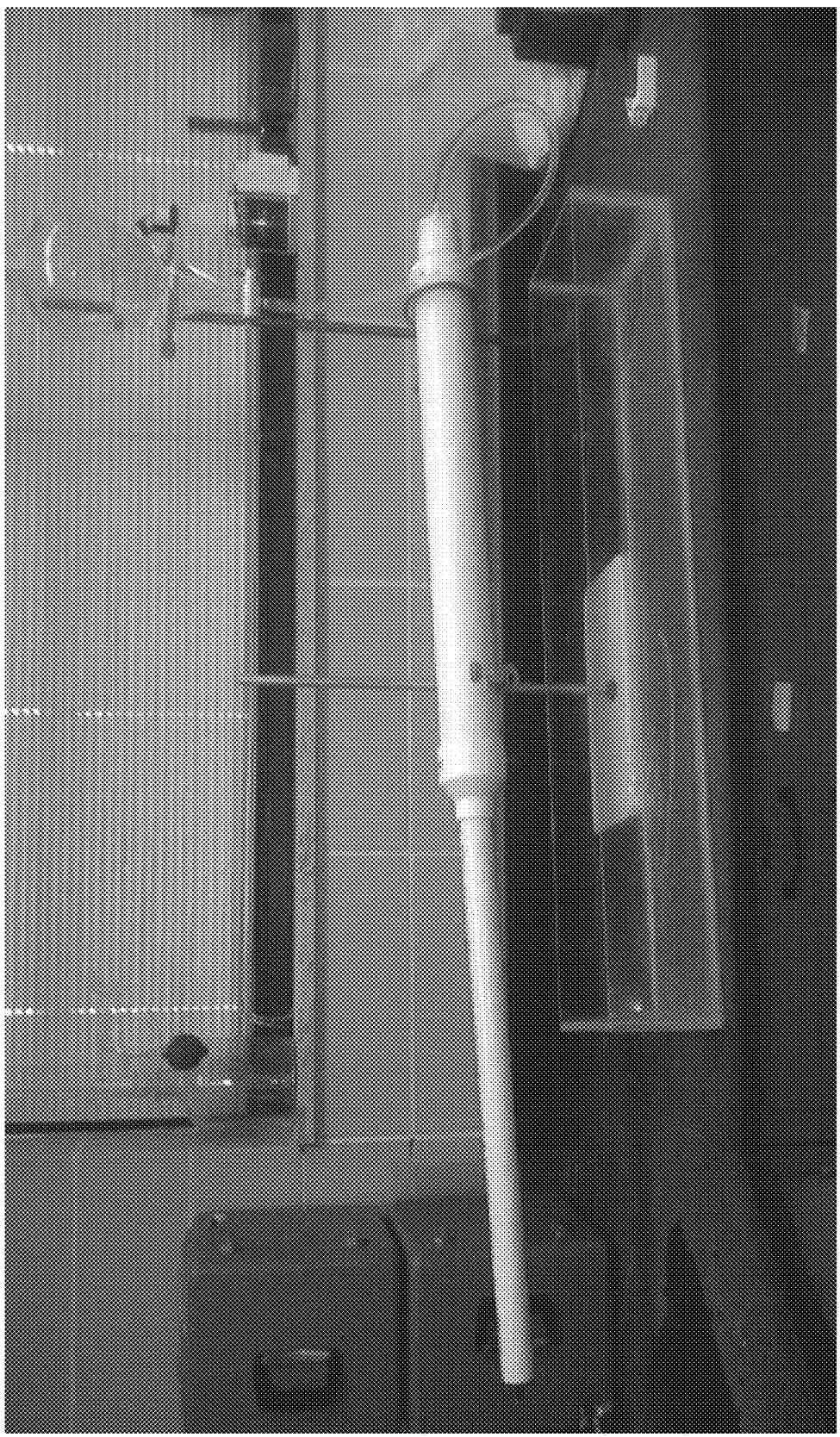
FIG. 5 illustrates a bench scale test for testing the effectiveness of UV light as a disinfectant for a pipe, in accordance with an embodiment of the present invention.

FIG. 4 illustrates a petri dish with a water sample taken after UV light has been applied to a pipe. In accordance with embodiments of the present invention, UV light is used as the disinfecting agent, instead of chlorine. To test the use of UV light as a method of disinfection, a small UV light was attached to sterile tubing and pulled through the three-foot section of contaminated PVC pipe at a rate of 1 foot per minute. The bench scale test is illustrated in FIG. 5. Sample results after filling the pipe with tap water and sampling were acceptable with no coliform or non-coliform bacteria. The tap water used in this experiment was chloraminated water rather than water with free chlorine. Free chlorine water would be more likely to cause some disinfection during the short contact time with the pipe than chloraminated would. As such, the UV light was found to inactivate bacteria. The exemplary test method below describes the testing that was performed in the bench scale pipe shown in FIG. 5.

Exemplary Test Method

As mentioned, FIG. 5 illustrates a small-scale model for testing purposes. A short section (three feet) of three-inch PVC pipe is attached by a reducer to a one-and-a-half inch pipe that is also three feet in length. At the front end is a small barbed ferule that allows for the flow of a contaminated solution. A standard solution of spiked water is used to contaminate the main prior to each testing procedure. The testing procedure is as follows:

(1) The pipe is filled with sterile water and is flushed with tap water (e.g., tap water that is chloraminated rather than having free chlorine) (Sample 1). Sample 1 must pass bacteriological testing. Otherwise, it is repeated. This test is performed to ensure the pipe is free of bacteria prior to the next steps.

(2) The pipe is filled with contaminated water (coliform and non-coliform isolates) and flushed with tap water (Sample 2). This test yields a background level of bacteria present.

(3) If Sample 2 fails bacteriological tests, the pipe is filled with super-chlorinated water to simulate the current disinfection practice (Sample 3).

(4) If Sample 3 passes bacteriological tests, the pipe will again be filled with contaminated water and flushed with tap water (Sample 4). This test is performed to establish a background level of bacteria present.

(5) If Sample 4 fails bacteriological testing, the pipe will have a UV light passed through the main at one minute per foot and then filled with tap water (Sample 5). This test will examine the effectiveness of the new disinfection procedure.

Tests Performed With Results

Test #1 (May 14, 2012: Single Scenario)

(1) Ran unaltered raw water through apparatus to contaminate pipe.

(2) Ran tap water from lab sink through the apparatus. Took one sample for membrane filtration (MF) and heterotropic plate count (HPC) to confirm contamination, such as to test for bacterial growth including total coliform (TC). Used 25% bleach to disinfect connections, tubing, Separatory Funnel, Stop Cock, and rubber stopper, (3) Passed UV light through main pipe at a rate of 1 ft/min. UV light automatically turned off after 90 seconds. Turned the light back on and re-ran the last quarter section of pipe.

(4) Ran tap water from lab sink through the apparatus. Took one sample for MF and HPC to test for bacterial growth including TC.

(5) Results:
a) MF before UV=0 TC 92 Atypical colonies
b) MF after UV=0 TC 71 Atypicals colonies
c) HPC before UV=31 CFU
d) HPC after UV=22 CFU Test #2 (May 16, 2012: Two Scenarios)
Scenario 1:

(1) Ran double filtered raw water through apparatus to contaminate pipe. Took Colilert 18 sample (the sample was collected in a sterile bottle for analysis using the Colilert-18 methodology, a presence/absence testing methodology) to confirm TC and *E. Coli*. Took another sample for MF and HPC for confirmation. Used 25% bleach solution to disinfect the connections, tubing, Separatory Funnel, stop cock, and rubber stopper.

(2) Passed UV light through main pipe at a rate of 1 ft/45 sec.

(3) Collected 1 L of Tap 2 and ran through apparatus. Took Colilert 18 sample to test for TC and *E. Coli*. Took another sample for MF and HPC to test for bacterial growth including TC.

(4) Results:
a) Colilert 18:
  Contaminated sample=Present/*E. Coli*
  T2 after UV=Absent
b) Membrane Filtration:
  Contaminated sample=17 TC
  Too Numerous To Count (TNTC)=Atypical colonies (colonies that are non-coliform bacteria)
  T2 after UV=0 TC, 0 Atypical colonies
  Blank=0 TC, 0 Atypical colonies
c) HPC:
  Contaminated sample=TNTC
  T2 after UV=1

Scenario 2:

(1) Ran diluted raw water (20 mL raw/980 mL DI) through apparatus to contaminate pipe. Took Colilert 18 sample to confirm TC and *E. Coli*. Took another sample for Membrane Filtration and HPC for confirmation. Used 25% bleach solution to disinfect the connections, tubing, Separatory Funnel, stop cock, and rubber stopper.

(2) Passed UV light through main pipe at a rate of 1 ft/45 sec.

(3) Collected 1L of Tap 2 and ran through apparatus. Took Colilert 18 sample to test for TC and *E. Coli*. Took another sample for MF and HPC to test for bacterial growth including TC.

(4) Results:
a) Colilert 18:
  Contaminated sample=Present/*E. Coli*
  T2 after UV=Absent but cloudy
b) Membrane Filtration:
  Contaminated sample=11 TC, TNTC Atypical coloniees
  T2 after UV=0 TC, 10 Atypical colonies
  Blank=0 TC, 0 Atypical colonies
c) HPC:
  Contaminated sample=148
  T2 after UV=0
d) Daily Tap 2 results
  Membrane Filtration: 0 TC, 2 Atypical colonies
  HPC: 0

Test #3 (Jun. 7, 2012):

(1) Ran double filtered raw water through apparatus to contaminate pipe. Took Colilert 18 sample to confirm TC and *E. Coli*. Took another sample for Membrane Filtration and HPC for confirmation. Used 100 ppm bleach solution to disinfect the connections, tubing, Separatory Funnel, stop cock, and rubber stopper. The connection, tubing, stop cock, and rubber stopper were submerged in the bleach solution for 5 min. The Separatory Funnel was swirled with bleach for 5 min.

(2) Passed UV light through main pipe at a rate of 1 ft/45 sec.

(3) Collected 1 L of Tap 2 and ran through apparatus. Took Colilert 18 sample to test for TC and *E. Coli*. Took another sample for MF and HPC to test for bacterial growth including TC.

(4) Results:
a) Colilert 18:
  Contaminated sample=Present/Not *E. Coli*
  T2 after UV=Absent
b) Membrane Filtration:
c) Contaminated sample=7 TC, TNTC Atypical colonies
  T2 after UV=0 TC, 0 Atypical colonies
  Blank=0 TC, 0 Atypical colonies
d) HPC:
  Contaminated sample=Confluent Growth
  T2 after UV=0
e) Daily T2 Results:
  Membrane Filtration=0 TC, 8 Atypical colonies
  HPC=1

Test #4 (Jun. 11, 2012):

(1) Ran double filtered raw water through apparatus to contaminate pipe. Took Colilert 18 sample to confirm TC and *E. Coli*. Took another sample for Membrane Filtration and HPC for confirmation. Used 100 ppm bleach solution to disinfect the connections, tubing, Separatory Funnel, stop cock, and rubber stopper. The connection, tubing, stop cock, and rubber stopper were submerged in the bleach solution for 5 min. The Separatory Funnel was swirled with bleach for 5 min.

(2) Passed UV light through main pipe at a rate of 1 ft/45 sec.

Figure 6:
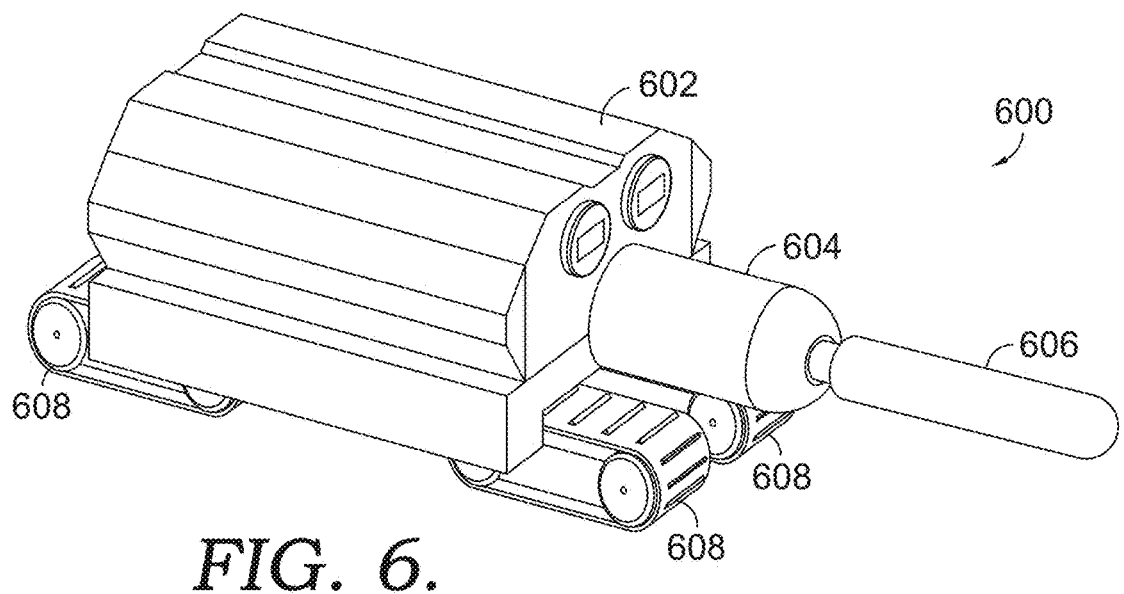
FIG. 6 illustrates a remotely controlled device for transporting a UV light source through a pipe, in accordance with an embodiment of the present invention.

(3) Collected 1 L of Tap 2 and ran through apparatus. Took Colilert 18 sample to test for TC and *E. Coli*. Took another sample for MF and HPC to test for bacterial growth including TC.
(4) Results:
a) Colilert 18:
Contaminated sample=Present/Not *E. Coli*
T2 after UV=Absent
b) Membrane Filtration:
Contaminated sample=0 TC, 145 Atypical colonies
T2 after UV=0 TC, 23 Atypical colonies
Blank=0 TC, 0 Atypical colonies
c) HPC:
Contaminated sample=TNTC
T2 after UV=184
d) Daily Tap 2 Results:
Membrane Filtration=0 TC, 1 Atypical colony
HPC=0
Test #5 (Jun. 18, 2012):
(1) Ran diluted raw water (50 mL/950 mL) through apparatus to contaminate the pipe. Took Colilert 18 sample to confirm TC and *E. Coli*. Took another sample for Membrane Filtration and HPC for confirmation. Used 100 ppm bleach solution to disinfect the connections, tubing, Separatory Funnel, stop cock, and rubber stopper. The connections, tubing, stop cock, and rubber stopper were submerged in the bleach solution for 5 min. The Separatory Funnel was swirled with bleach.
(2) Passed UV light through main pipe at a rate of 1 ft/45 sec.
(3) Collected 1 L of Tap 2 and ran through apparatus. Took Colilert 18 sample to test for TC and *E. Coli*. Took another sample for MF and HPC to test for bacterial growth including TC.
(4) Results:
a) Colilert 18:
Contaminated sample=Present/*E. Coli*
T2 after UV=Present/Not *E. Coli*
b) Membrane Filtration:
Contaminated sample=6 TC, TNTC Atypical colonies
T2 after UV=0 TC, 52 Atypical colonies
Blank=0 TC, 0 Atypical colonies
c) HPC:
Contaminated sample=149
T2 after UV=TNTC
d) Daily Tap 2 Results:
Membrane Filtration=0 TC, 3 Atypical colonies
HPC=0
e) T2 sample after UV was most likely contaminated due to shortened disinfection time of all components with the bleach solution.
Test #6 (Jun. 19, 2012):
(1) Ran diluted raw water (50 mL/950 mL) through apparatus to contaminate the pipe. Took Colilert 18 sample to confirm TC and *E. Coli*. Took another sample for Membrane Filtration and HPC for confirmation. Used 100 ppm bleach solution to disinfect the connections, tubing, Separatory Funnel, stop cock, and rubber stopper. The connections, tubing, stop cock, and rubber stopper were submerged in the bleach solution for 3-5 min. The Separatory Funnel was swirled with bleach.
(2) Passed UV light through main pipe at a rate of 1 ft/45 sec.
(3) Collected 1 L of Tap 2 and ran through apparatus. Took Colilert 18 sample to test for TC and *E. Coli*. Took another sample for MF and HPC to test for bacterial growth including TC.
(4) Results:
a) Colilert 18:
Contaminated sample=Present/*E. Coli*
T2 after UV=Absent
b) Membrane Filtration:
Contaminated sample=22 TC, TNTC Atypical colonies
T2 after UV=0 TC, 3 Atypical colonies
Blank=0 TC, 0 Atypical colonies
c) HPC:
Contaminated sample=106
T2 after UV=146
d) Daily Tap 2 Results:
Membrane Filtration=0 TC, 5 Atypical colonies
Test #7 (Jun. 21, 2012):
(1) Ran diluted raw water (50 mL/950 mL) through apparatus to contaminate the pipe. Took Colilert 18 sample to confirm TC and *E. Coli*. Took another sample for Membrane Filtration and HPC for confirmation. Used 100 ppm bleach solution to disinfect the connections, tubing, Separatory Funnel, stop cock, and rubber stopper. The connections, tubing, stop cock, and rubber stopper were submerged in the bleach solution for 5 min. The Separatory Funnel was swirled with bleach for 5 min.
(2) Passed UV light through main pipe at a rate of 1 ft/45 sec.
(3) Collected 1 L of Tap 2 and ran through apparatus. Took Colilert 18 sample to test for TC and *E. Coli*. Took another sample for MF and HPC to test for bacterial growth including TC.
(4) Results:
a) Colilert 18:
Contaminated sample=Present/Not *E. Coli*
T2 after UV=Absent
b) Membrane Filtration:
Contaminated sample=11 TC, TNTC Atypical colonies
T2 after UV=0 TC, 0 Atypical colonies
Blank=0 TC, 0 Atypical colonies
c) HPC:
Contaminated sample=197
T2 after UV=7
d) Daily Tap 2 Results:
Membrane Filtration=0 TC, 2 Atypical colonies Returning back to the figures, and particularly to FIG. 6, a remotely controlled device 600 for transporting a UV light source through a pipe is illustrated, in accordance with an embodiment of the present invention. Initially, various types and forms of remotely controlled devices may be used with embodiments of the present invention. Several types will be described herein, but that description is not exhaustive. Other types and forms of remotely controlled devices are contemplated to be within the scope of the present invention. The remotely controlled device shown in FIG. 6 includes a body portion 602, a light coupler 604, and movable mechanisms 608. The movable mechanisms 608 in the embodiment of FIG. 6 are tracks that roll through the interior portion of a pipe. Of course, tracks are just one example of movable mechanisms 608 that could be used. Other examples include wheels, spinning wheels, or a rounded object that is built to reduce friction between the movable mechanisms 608 and the interior surface of the pipe. The UV light 606 is coupled to the body portion 602 by way of the light coupler 604, which extends the UV light 606 in front of the remotely controlled device so that the UV light is omni-directional, providing a dosage of light to all interior surfaces of the pipe by which the UV light passes. In an alternative embodiment, the UV light 606 may be located on top of the remotely controlled device, or may even be located behind the device. In one embodiment, one UV light 606 is used with the remotely controlled device 600, but in another embodiment, such as where the pipe diameter is larger, multiple UV lights may be used in a single remotely controlled device 600 to move the light sources closer to the interior walls of the pipe.

In one embodiment, the remotely controlled device travels through the pipe wirelessly, not being tethered to anything. In this embodiment, a drive may be mechanically coupled to the movement mechanisms 608 to cause the remotely controlled device to move through the pipe. A motor may also be used in addition to the drive. In an alternative embodiment, the remotely controlled device is connected to a winch having a cable that is also connected to the remotely controlled device. The winch may operate manually, or may have a motor that operates the winch. The winch will be described in more detail herein with respect to FIG. 10. The remotely controlled device may be controlled at a remote location, such as outside the pipe. In this scenario, a person may have a remote control that is used to determine the rate at which the remotely controlled device travels through the pipe. Alternatively, the remotely controlled device may include software that allows for the device to operate on its own without human intervention. For instance, the device may be programmed with a rate at which it is to travel through the pipe. Information inputted into the device may also include a length of the pipe, pipe diameter, etc.

Figure 7:
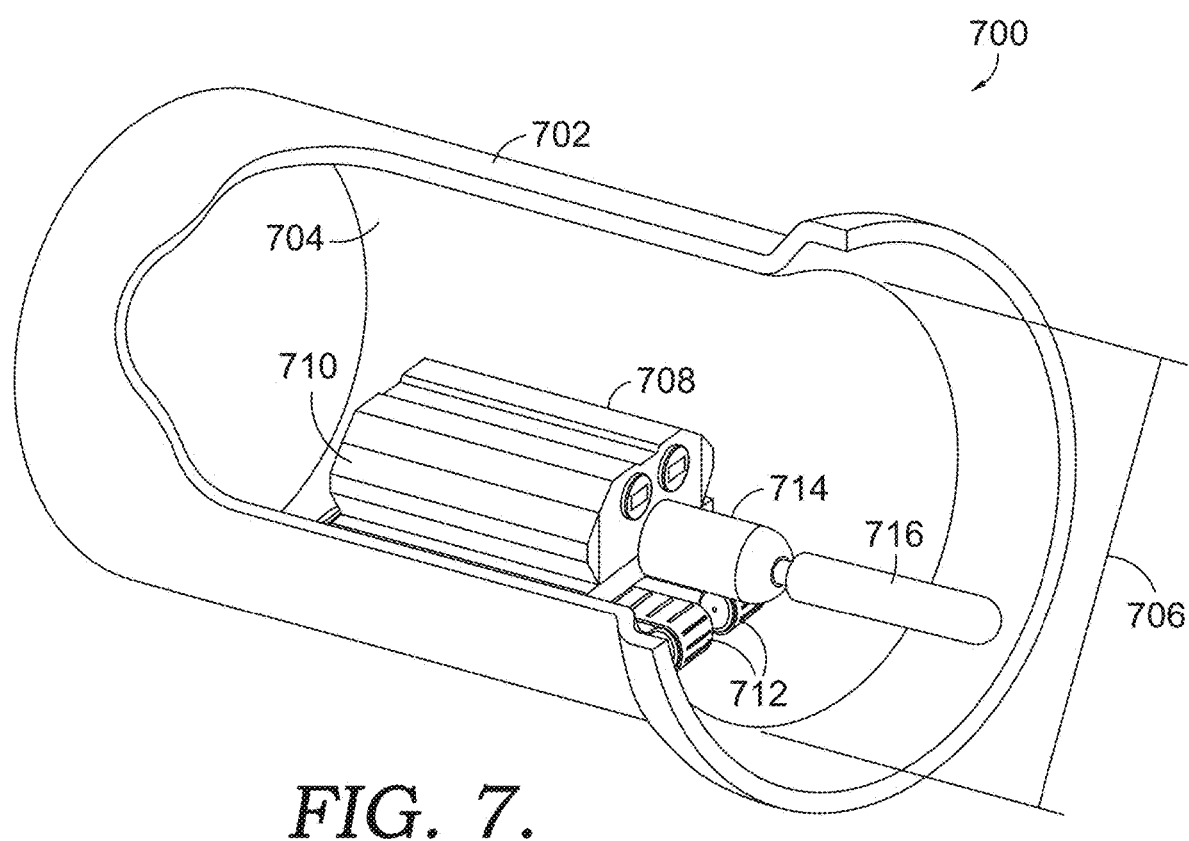
FIG. 7 illustrates a section view of a pipe with a remotely controlled device inside the pipe for transporting a UV light source, in accordance with an embodiment of the present invention.

FIG. 7 illustrates a section view 700 of a pipe with a remotely controlled device inside the pipe for transporting a UV light source, in accordance with an embodiment of the present invention. As mentioned, many different remotely controlled devices may be used, and the one illustrated in FIG. 7 is shown for illustrative purposes only. The pipe 702 has an interior surface 704, and has a diameter illustrated by item 706. The diameter 706 of the pipe 702 may be used to determine the frequency and intensity of the UV light used, and may also be used to determine how fast the remotely controlled device is to move through the pipe. Here, the remotely controlled device 708 has a top portion 710, a light coupler 714 attached to the UV light 716, and movement mechanisms 712.

Figure 8:
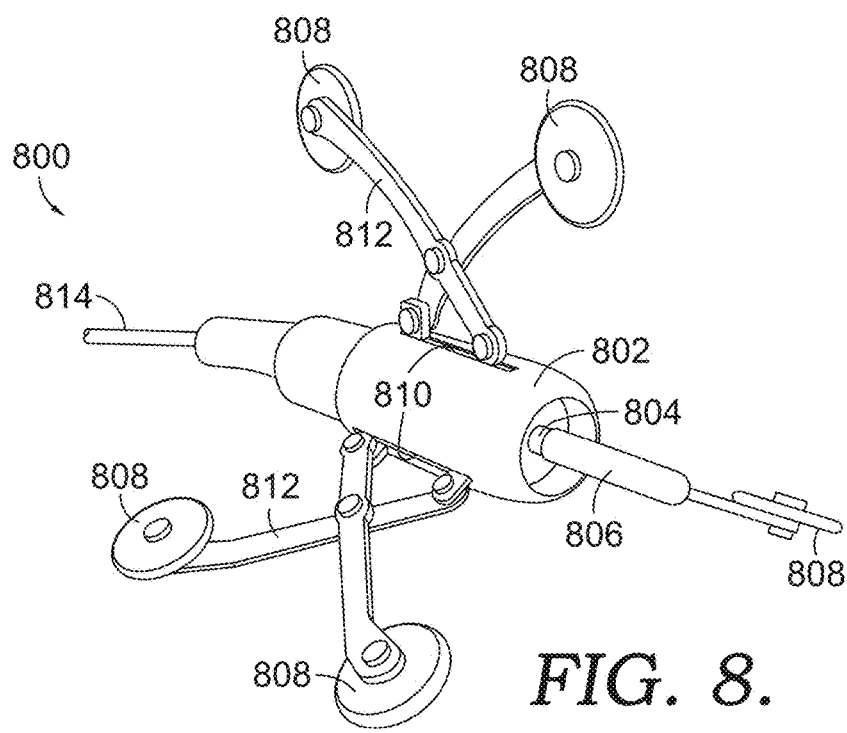
FIG. 8 illustrates a remotely controlled device for transporting a UV light source through a pipe, in accordance with an embodiment of the present invention.

FIG. 8 illustrates another remotely controlled device 800 for transporting a UV light source through a pipe, in accordance with an embodiment of the present invention. As previously mentioned, the remotely controlled devices shown and described herein are provided for exemplary purposes only. Other devices are contemplated to be within the scope of the present invention. The remotely controlled device 800 includes a body portion 802, a light coupler 804 for attaching the UV light source 806 to the remotely controlled device 800, and movement mechanisms 808. The body portion 802 is mechanically coupled to the UV light source 806 so that the UV light source 806 remains centered within the water main as the remotely controlled device 800 moves axially through the water main. In one instance, the UV light source 806 is mounted to a top portion of the body portion 802, but in another instance, is mounted to a front portion of the body portion 802. As mentioned, there may be one UV light source 806 mounted to the body portion 802, but in some embodiments, more than one UV light source 806 is used to ensure all interior walls of the pipe are disinfected, which may be the case for larger diameter pipes. The movement mechanisms 808 in the embodiment of FIG. 8 are wheels that rotate when the remotely controlled device is moved through the pipe. Here, the movement mechanisms 808 are secured to the body portion 802 by attachment members 812. The attachment members 812 are secured to the body portion 802 by way of a movement slot 810 that allows the attachment members 812 to slide either closer to each other or apart from each other. The movement slot 810 allows the remotely controlled device 800 to adapt to either smaller or larger diameter pipes. For instance, embodiments of the present invention can be used in conjunction with small mains (e.g., 4 inches, 6 inches) and larger mains (e.g., 20 inches). The portion of the attachment members 812 that makes contact with the movement slot 810 may be a movable pivot point so that it can pivot to adjust based on the size of the pipe. The adjustment of the attachment members 812 to fit different pipe sizes may be accomplished by using tension, a spring, compression, or the like.

Also included on the remotely controlled device 800 is a tether 814 that can be used, in some embodiments, to connect the remotely controlled device 800 to a winch, which will be discussed further herein. As mentioned, the tether 814 may be coupled to the body portion 802, and may be provided for physical manipulation of the remotely controlled device, such as when a winch is utilized. Alternatively, the tether 814 illustrated in FIG. 8 may be for transmission of control signals to or from the remotely controlled device. Even further, the tether 814 may be used for video relay from the remotely controlled device. In this embodiment, the remotely controlled device may include one or more cameras for capturing video as the device moves through the pipe. Alternative to or in addition to the cameras, one or more flashlights may be mounted to the remotely controlled device. In one embodiment, a winch may not be used to physically manipulate the movement of the remotely controlled device, and instead, a drive is mechanically coupled to the plurality of movement mechanisms that causes the remotely controlled device to move through the water main. The drive may be driven by one of many different forms of energy, and as such, may be operated pneumatically, hydraulically, etc.

In the embodiment of FIG. 8, the UV light source outputs omni-directional light such that as the remotely controlled device 800 moves axially through the water main, the interior surfaces of the water main are contacted by the UV light as the UV light passes by these surfaces. As such, the top, bottom, and side portions of the interior surface of the pipe all receive a substantially equal dosage of the UV light.

In one embodiment, the remotely controlled device requires a power source. In this case, the power source may be electric, and as such the device may have a power cord attached thereto. Alternatively, a portable power supply, such as a battery, may be used to power the remotely controlled device. In other embodiments, the remotely controlled device may not require a power source. Here, the UV light source may have its own power source such that the remotely controlled device does not need one.

Figure 9:
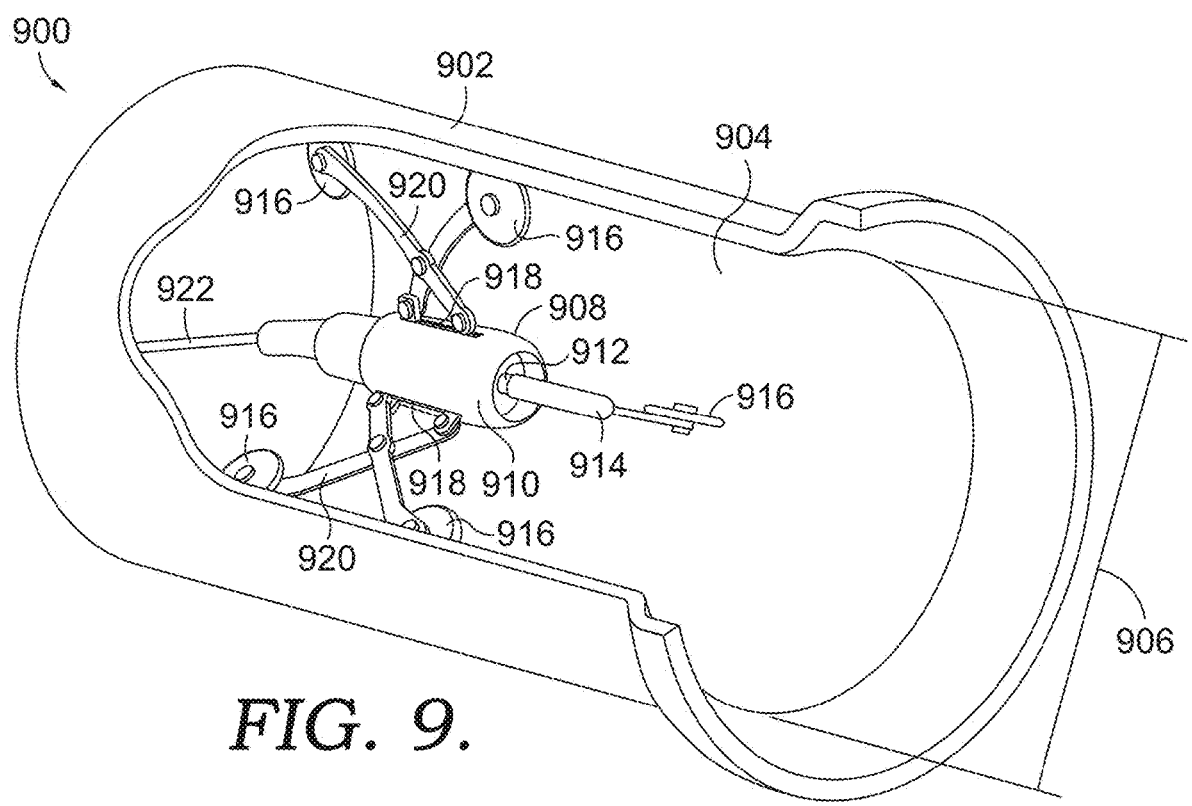
FIG. 9 illustrates a section view of a pipe with a remotely controlled device inside the pipe for transporting a UV light source, in accordance with an embodiment of the present invention.

FIG. 9 illustrates a section view 900 of a pipe with a remotely controlled device inside the pipe for transporting a UV light source, in accordance with an embodiment of the present invention. The remotely controlled device illustrated in FIG. 9 is similar to the device of FIG. 8. Here, the pipe 902 includes an interior surface 904 and a diameter, represented by item 906. The remotely controlled device 908 includes a body portion 910, a light coupler 912 that connects the body portion 910 to the UV light 914, and movement mechanisms 916. Here, the movement mechanisms 916 are secured to the body portion 910 by attachment members 920. The attachment members 920 are secured to the body portion 910 by way of a movement slot 918 that allows the attachment members 920 to slide either closer to each other or apart from each other. The movement slot 918 allows the remotely controlled device 908 to adapt to either smaller or larger diameter pipes. The tether 922 is illustrated for use by a winch, which controls the forward and reverse movement of the remotely controlled device through the pipe. In one embodiment, the remotely controlled device is not tethered to a winch, and thus may operate wirelessly and without cords and tethers. In this instance, a drive, which may be attached to a motor, may be mechanically coupled to the movement mechanisms.

Figure 10:
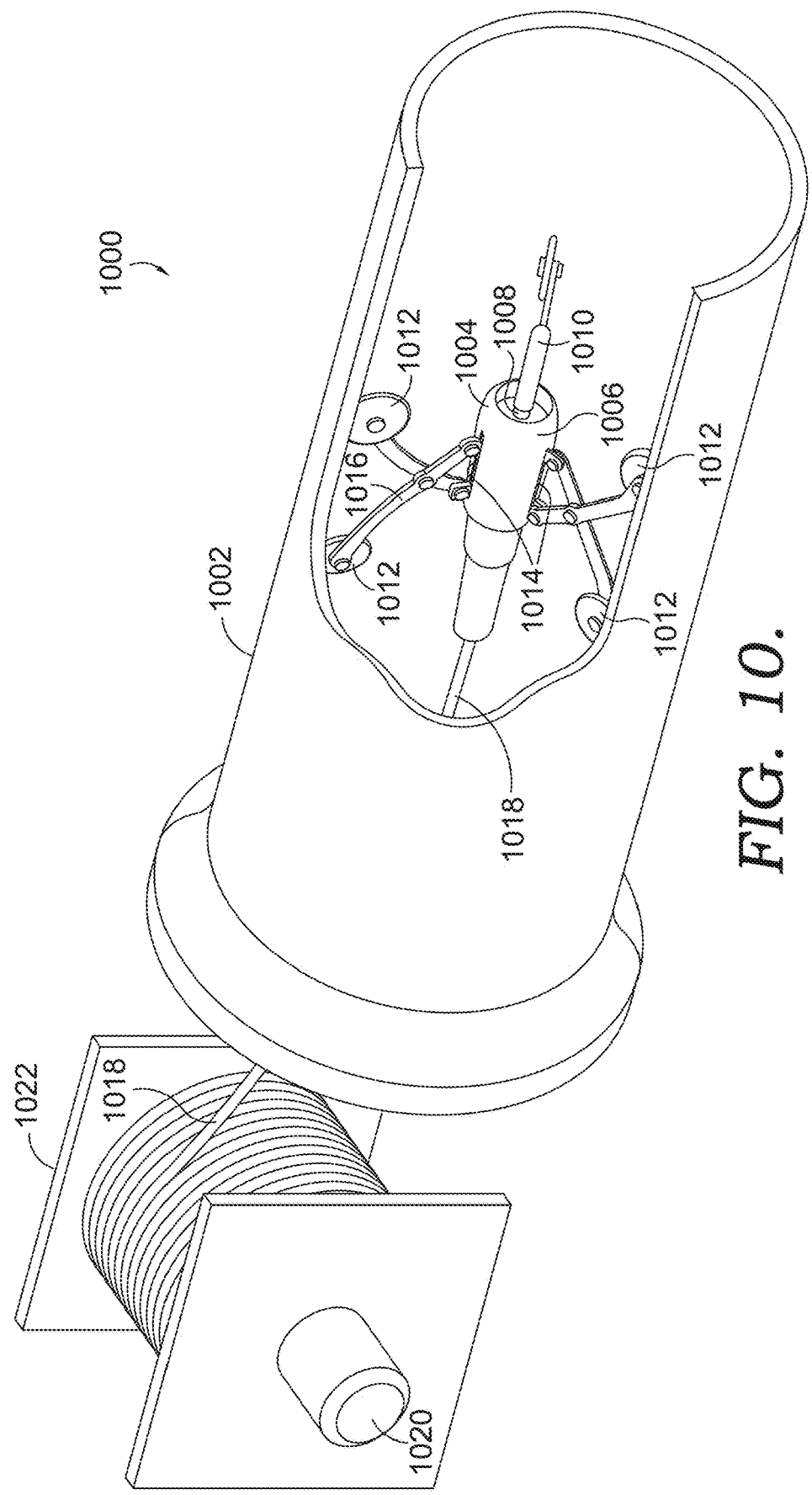
FIG. 10 illustrates a section view of a pipe with a remotely controlled device inside the pipe and a winch for transporting a UV light source, in accordance with an embodiment of the present invention.

FIG. 10 illustrates a section view of a pipe with a remotely controlled device inside the pipe and a winch for transporting a UV light source, in accordance with an embodiment of the present invention. The remotely controlled device 1004 is located within the pipe 1002, and includes a body portion 1006, a light coupler 1008 that attaches the UV light 1010 to the remotely controlled device 1004, and movement mechanisms 1012. Here, the movement mechanisms 1012 are secured to the body portion 1006 by attachment members 1016. The attachment members 1016 are secured to the body portion 1006 by way of a movement slot 1014 that allows the attachment members 1016 to slide either closer to each other or apart from each other. The movement slot 1014 allows the remotely controlled device 1004 to adapt to either smaller or larger diameter pipes. The remotely controlled device 1004 has a tether 1018, which in this embodiment, may be a cable that attaches it to a winch 1022. The winch 1022 also may have a drive and a motor 1020 that turns the winch in one direction to move the remotely controlled device in a forward direction, and that turns the winch in a different direction to move the remotely controlled device in a reverse direction. This allows the remotely controlled device to be tethered to an object outside of the pipe, and still allows it to be remotely controlled from a location outside of the pipe. A winch may take on many forms. For instance, the winch may be secured to the pipe itself, or may be a standalone object. Many times, the winch is contained within a box or some other protective covering, although not shown here in FIG. 10.

Figure 11:
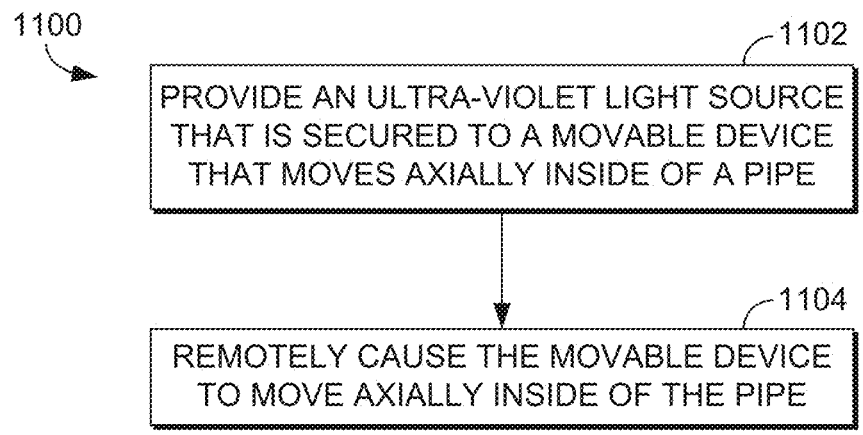
FIG. 11 illustrates a flow diagram of a method for disinfecting water mains using UV light.

FIG. 11 illustrates a flow diagram of a method 1100 for disinfecting water mains using UV light. A pipe, such as a water main, is typically disinfected prior to its use in transporting a substance from one location to another within the pipe. For instance, water main pipes transport water from one location to another location. Prior to transporting water, the water main is disinfected to kill any bacteria or other harmful organisms on the interior of the pipe.

Initially, a UV light source is provided at step 1102 that is secured to a movable device that moves axially inside of a pipe. The UV light source is selected based on various characteristics, including its frequency and intensity. Characteristics of the pipe are taken into consideration when the frequency and intensity of the UV light source are determined. These characteristics may include the material of the pipe and the size (e.g., diameter) of the pipe. For example, a smaller pipe may require a UV light source having a lower frequency and intensity than that required for a larger pipe. The UV light source may provide a pulsed emission of light in one embodiment, but in an alternative embodiment, may provide a continuous emission of light.

UV light is electromagnetic radiation with a wavelength shorter than that of visible light, and is in the range between 10 nm and 400 nm, which corresponds to photon energies from 3 eV to 124 eV. Although UV light is found in natural sources, such as sunlight, it is also found in artificial sources, including black lights, short wave UV lamps, gas-discharge lamps, UV LEDs, and UV lasers. The germicidal effectiveness curve (i.e., effectiveness for UV absorption by DNA) has two peaks. The first peak is about 185 nm, and the other is about 265 nm. As such, UV light having a wavelength of between 100 nm to 280 nm is typically the range used to sterilize surfaces and kill organisms on those surfaces. As such, in one embodiment, the UV light source used is a low-pressure mercury-vapor lamp, which emits about 86% of its light at 254 nm, which is close to the second peak mentioned above. UV light at these germicidal wavelengths causes adjacent thymine molecules on DNA to dimerize. If enough of these defects accumulate on a microorganism's DNA, its replication is inhibited, thereby rendering it harmless. The wavelength range of UV light used in embodiments described herein is 100 nm to 400 nm, and more specifically, between 100 nm and 280 nm.

At step 1104, the movable device is remotely caused to move axially inside of the pipe at a rate that is determined based on one or more characteristics of the pipe. These characteristics may include a size and material of a pipe, so that the interior surface of the pipe receives the appropriate dosage of UV light as the movable device moves axially in the pipe. As used herein, the dosage of UV light is dictated by the frequency and intensity of the UV light, and the rate of the movable device through the pipe, and refers to quantity of photons emitted from the UV light source. As the UV light source moves in the pipe, the interior surface of the pipe is disinfected, thereby killing harmful organisms. It should be noted that instead of a surface moving by a stationary UV light source, here, the UV light source is moving and the surface is stationary.

The length of the pipe may be determined, and may be used to know how far into the pipe the movable device is to travel before returning to the starting point. In one embodiment, the movable device includes a body portion that is mechanically coupled to the UV light source, and movement mechanisms that are coupled to the body portion for moving the automated device axially through the pipe. The movement portions may be any type of mechanisms that can move along a pipe, including wheels, rollers, tracks, or some other mechanism that is rounded and can easily slide along the interior surface of the pipe at a reduced friction. The movable device may be coupled to a winch by way of a cable so that the winch causes the movable device to move in a forward direction and a reverse direction through the pipe, depending on whether the movable device is moving away from the winch, thus disinfecting the pipe, or moving toward the winch, moving toward its starting position. The winch may be driven by a motor and a drive shaft that allows the movable device to be remotely controlled. For instance, an operator may control the movement of the movable device by controlling the winch.

In one embodiment, the remotely controlled device includes a detector that can detect if the UV light has failed such as if the light bulb burned out while traveling through the pipe. The remotely controlled device may have an alarm that goes off if the UV light has somehow failed, or may send a signal back to a controller that would allow the operator to know that the UV light has failed. This feature would allow the operator to know to repair the issue, such as install a new UV light source, so that the interior of the pipe can be adequately disinfected.

Figure 12:
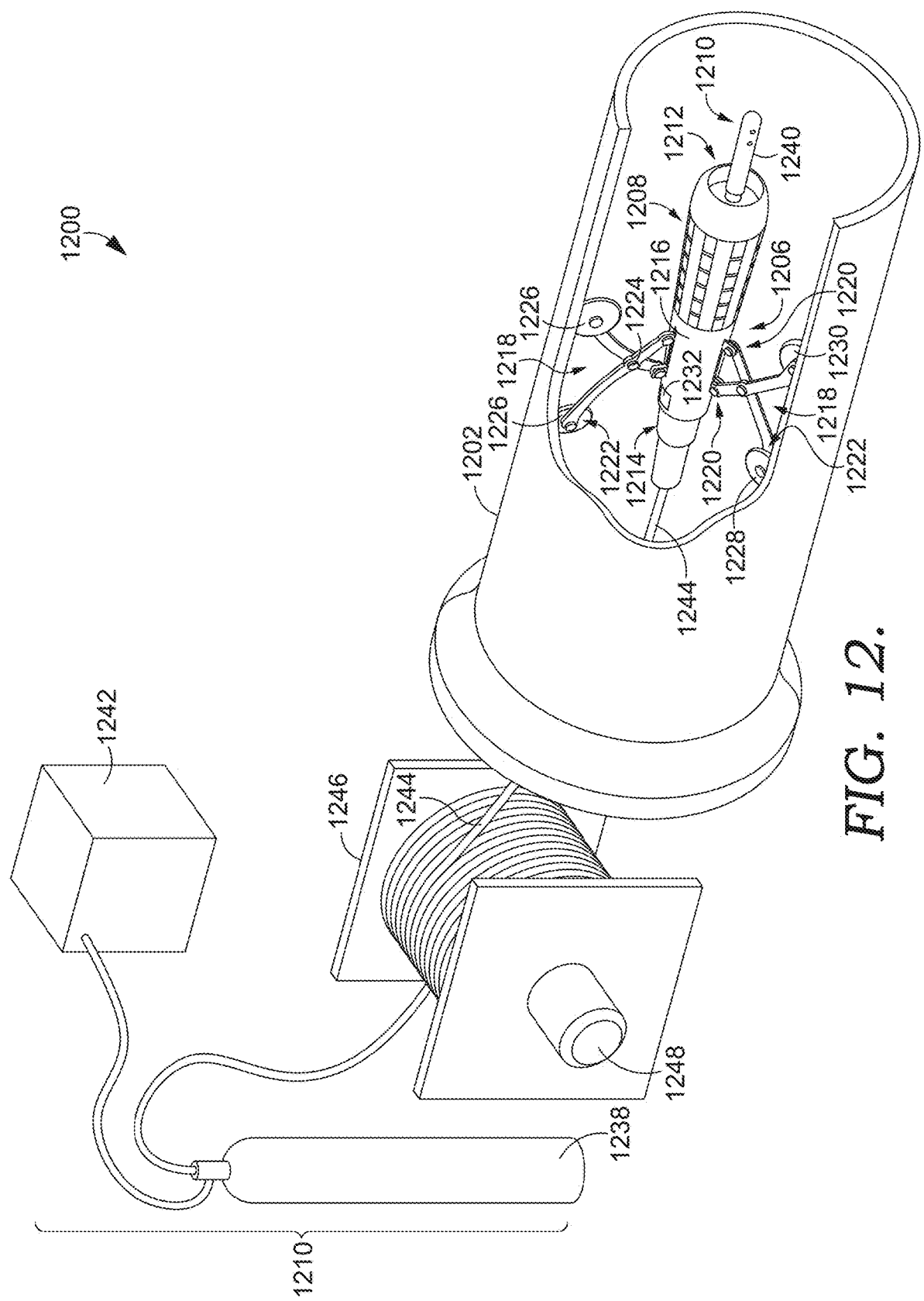
FIG. 12 illustrates a remotely controlled device, in accordance with an embodiment of the present invention.

Other aspects of systems and methods for disinfecting water mains will now be described in reference to FIGS. 12-15. Referring initially to FIG. 12, a water main disinfecting system 1200 may include a pipe 1202 having an interior surface 1204, a remotely-controlled carriage 1206, at least one UV light source 1208 and an oxidant supply component 1210.

In some aspects, the remotely controlled carriage 1206 may include the movable device and/or the remotely controlled device as described above in reference to FIGS. 6-10. In other aspects, the remotely-controlled carriage 1206 may include a forward end 1212 opposite a rearward end 1214 and be configured to couple with the at least one UV light source 1208 and move axially inside of the pipe 1202. The remotely-controlled carriage 1206 may have a body portion 1216, a plurality of legs extending away from the body portion 1216 to one of a plurality of contact members 1226. Each leg may have a first end 1220 opposite a second end 1222 and may be coupled proximate the first end 1220 to the body portion 1216 and proximate the second end to one of the plurality of contact members 1226. The legs may be coupled to the body portion 1216 in a manner that allows the legs to adjust (e.g., slide, fold, twist, bend, etc.) for different sized pipes 1202. In some aspects, each leg of the plurality of legs is paired with another leg to form a pair of legs 1218. For example, in the illustrated embodiment a plurality of pairs of legs 1218 are shown. Each pair of the plurality of pairs of legs 1218 may be pinned together with a pin 1224 intermediate to the first end 1220 and the second end 1222 of each respective leg. In the illustrated embodiment, each pair of the plurality of pairs of legs 1218 comprises a scissor hinge that is configured to adjust the effective diameter of the remotely-controlled carriage 1206 to match an interior diameter of the pipe 1202.

The plurality of contact members 1226 are configured to contact the interior surface 1204 of the pipe 1202 and permit the remotely-controlled carriage 1206 to move axially through the pipe 1202. In some aspects, each pair of the plurality of pairs of legs 1218 is coupled to a single contact member. In other aspects, each leg is coupled to a single contact member, such as in the illustrated embodiment. Each pair of the plurality of pairs of legs 1218 may be coupled to a first contact member 1228 and to a second contact member 1230. In the illustrated embodiment, each pair of the plurality of pairs of legs 1218 has one leg coupled to the first contact member 1228 proximate the second end 1222 of the leg and has the other leg of the pair coupled to the second contact member 1230 proximate the second end 1222 of such other leg.

The remotely controlled carriage 1206 may further include a receiver 1232. The receiver 1232 may be configured to receive instructions from a remote controller. For example, the remote controller may be configured to send signals to the receiver 1232 and cause the remotely-controlled carriage 1206 to move axially inside of the pipe 1202. The remote controller may be a wireless controller, in accordance with some aspects. In other aspects, the remote controller may be coupled to the remotely controlled carriage 1206 (for e.g., with a tether 1244). Although only one tether 1244 is shown in FIG. 12, it is contemplated that a plurality of tethers may be used. For example, a first tether may be used to communicate signals from the remote controller to the receiver 1232 and a second tether may be used to communicate oxidizing agents to a dispensing component coupled to the remotely controlled carriage 1206 (as described below). In other words, the plurality of tethers may communicate information or materials into the pipe 1202 (whether or not to the remotely controlled carriage 1206) from outside of the pipe 1202. In other aspects, the tether 1244 may be used to push, pull or otherwise move the remotely controlled carriage 1206 inside the pipe 1202.

In some aspects, the remotely controlled carriage 1206 may be powered with batteries stored on board the remotely controlled carriage 1206. The batteries may be rechargeable. The remotely controlled carriage 1206 may be configured for wireless charging of the batteries.

Figure 13:
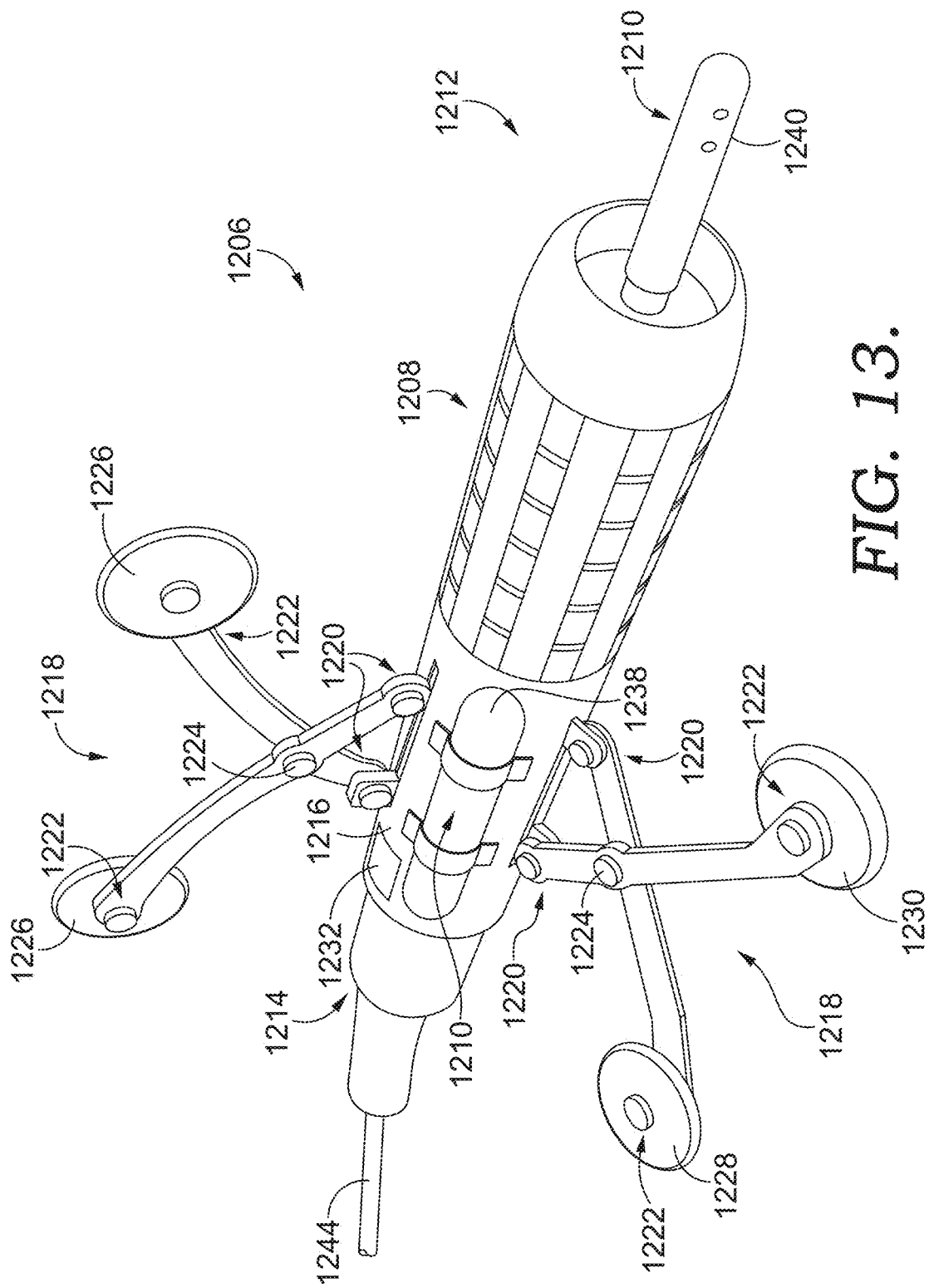
FIG. 13 illustrates a section view of a pipe with a remotely controlled device inside the pipe, in accordance with an embodiment of the present invention.

The at least one UV light source 1208 may include the UV light source described above. For example, the UV light source may output omni-directional UV light that travels from the at least one UV light source 1208 towards the interior surface 1204 of the pipe 1202 across an entire circumference of the pipe 1202. In other aspects, the at least one UV light source 1208 may include a plurality of UV light sources that are configured to act in combination to output UV light towards the interior surface 1204 of the pipe 1202 across an entire circumference of the pipe 1202. As illustrated in FIG. 13, the at least one light source 1208 may include a plurality of rows of UV lights and each of the plurality of rows may include a plurality of UV lights. Each of the plurality of rows of UV lights may be spaced around a perimeter of the body portion 1216. In some aspects, the dosage of the output UV light may be controlled by using only a portion of the UV lights in each of the plurality of rows of UV lights. In other aspects, the dosage of the output UV light may be controlled by using only a portion of the plurality of rows of UV lights. The at least one UV light source 1208 may emit UV light having a wavelength between 100 nanometers and 400 nanometers. In other aspects, the at least one UV light source 1208 may emit UV light having a wavelength less than 300 nanometers in order to irradiate primary oxidants within the pipe 1202.

The oxidant supply component 1210 may be configured to disinfect the pipe 1202 with an advanced oxidation process. For example, the oxidant supply component 1210 may dispense one or more oxidizing agents (e.g., oxygen ($O_2$), ozone ($O_3$) and/or hydrogen peroxide ($H_2O_2$)) into the pipe 1202. The dispensed oxidizing agents may oxidize any contaminants contacted within the pipe 1202.

The oxidant supply component 1210 may include a storage component 1238 for storing the oxidizing agents and a dispensing component 1240 in communication with the storage component 1238 and configured for dispensing the oxidizing agents into the pipe 1202. In the embodiment illustrated in FIG. 12, the storage component 1238 is maintained outside of the pipe 1202 and in communication with the dispensing component 1240 through the tether 1244. As discussed above, even though only one tether 1244 is illustrated in FIG. 12, it is contemplated that more than one tether 1244 may be employed to communicate the oxidizing agents, the signals from the remote controller, and any other information, substance or energy from outside the pipe 1202 to the remotely controlled carriage 1206 within the pipe 1202.

In the embodiment illustrated in FIG. 13, the storage component 1238 is coupled to the remotely controlled carriage 1206. The dispensing component 1240 may be coupled to the remotely controlled carriage 1206 and be in communication with the storage component 1238, as shown in the illustrated aspects. The dispensing component 1240 may be positioned nearer the forward end 1212 of the remotely controlled carriage 1206 than the at least one UV light source 1208. Hence, the oxidant supply component 1210 may operate in conjunction with the remotely controlled carriage 1206. In other aspects, the oxidant supply component 1210 may operate independently from the remotely controlled carriage 1206. For example, the oxidant supply component 1210 may not be coupled to the remotely controlled carriage 1206 and the dispensing component

1240 may be moved axially down the pipe 1202 independently of the remotely controlled carriage 1206.

In further aspects, the oxidant supply component 1210 may include an oxidizing agent generator 1242 configured to produce the oxidizing agents. The oxidizing agent generator 1242 may be in communication with the storage component 1238 (as illustrated in FIG. 12) or may be in communication directly with the dispensing component (not shown). For example, the oxidizing agent generator 1242 may comprise an ozone generation system that is capable of in situ generation of ozone. An exemplary ozone generation system could include the use of a UV lamp (e.g., a UV lamp emitting UV light at 185 nanometers), where air (or molecular oxygen dissolved in water) is passed over the UV lamp splitting the molecular oxygen ($O_2$) into individual oxygen atoms (O·), which then interact with molecular oxygen to create ozone ($O_3$). The at least one UV light source may comprise the UV lamp. Other conventional ozone generation systems or ozone sources known to one skilled in the art are also contemplated for use with the remotely-controlled carriage 1206 of the present disclosure.

In operation, the system described above may disinfect water mains in several ways. First, the at least one UV light source may emit UV light that in turn may irradiate contaminants located on the inner surface 1204 of the pipe 1202 or suspended within the pipe 1202 (e.g., suspended or dissolved in fluid, such as water, contained within the pipe 1202) (i.e., direct irradiation). Second, the oxidizing agents (e.g., oxygen ($O_2$), ozone ($O_3$) and/or hydrogen peroxide ($H_2O_2$)) emitted from the oxidant supply component 1210 may oxidize contaminants located on the inner surface 1204 of the pipe 1202 or suspended within the pipe 1202 (e.g., suspended or dissolved in fluid, such as water, contained within the pipe 1202) (i.e., oxidation by direct supply of oxidizing agents). Third, the emitted UV light may interact with at least a portion of the emitted oxidizing agents to generate additional oxidizing agents (e.g., the emitted UV light may convert a portion of the emitted hydrogen peroxide ($H_2O_2$) into ozone ($O_3$)) and the generated additional oxidizing agents may oxidize contaminants located on the inner surface 1204 of the pipe 1202 or contained within the pipe 1202 (e.g., suspended or dissolved in fluid, such as water, contained within the pipe 1202 and as described above) (i.e., oxidation by supplemental oxidizing agent generation). This list of ways the above system 1200 disinfects the pipe 1202 is provided for illustrative purposes and is not intended to be exhaustive.

In addition to disinfecting water mains, the above described system 1200 may also eliminate contaminants found in the fluid contained within the pipe 1202 through advanced oxidation processes. In some aspects, the oxidizing agents emitted from the oxidant supply component 1210 and/or the generated additional oxidizing agents may oxidize contaminants located on the inner surface 1204 of the pipe 1202 or contained within the pipe 1202 (e.g., suspended or dissolved in fluid, such as water, contained within the pipe 1202) (i.e., oxidation by direct supply of oxidizing agents). In other aspects, the emitted UV light may interact with the oxidizing agents emitted from the oxidant supply component 1210 and or the generated additional oxidizing agents to generate hydroxyl radicals (·OH), which oxidize contaminants located on the inner surface 1204 of the pipe 1202 or contained within the pipe 1202 (e.g., suspended or dissolved in fluid, such as water, contained within the pipe 1202) (i.e., oxidation by hydroxyl radical generation).

Figure 14:
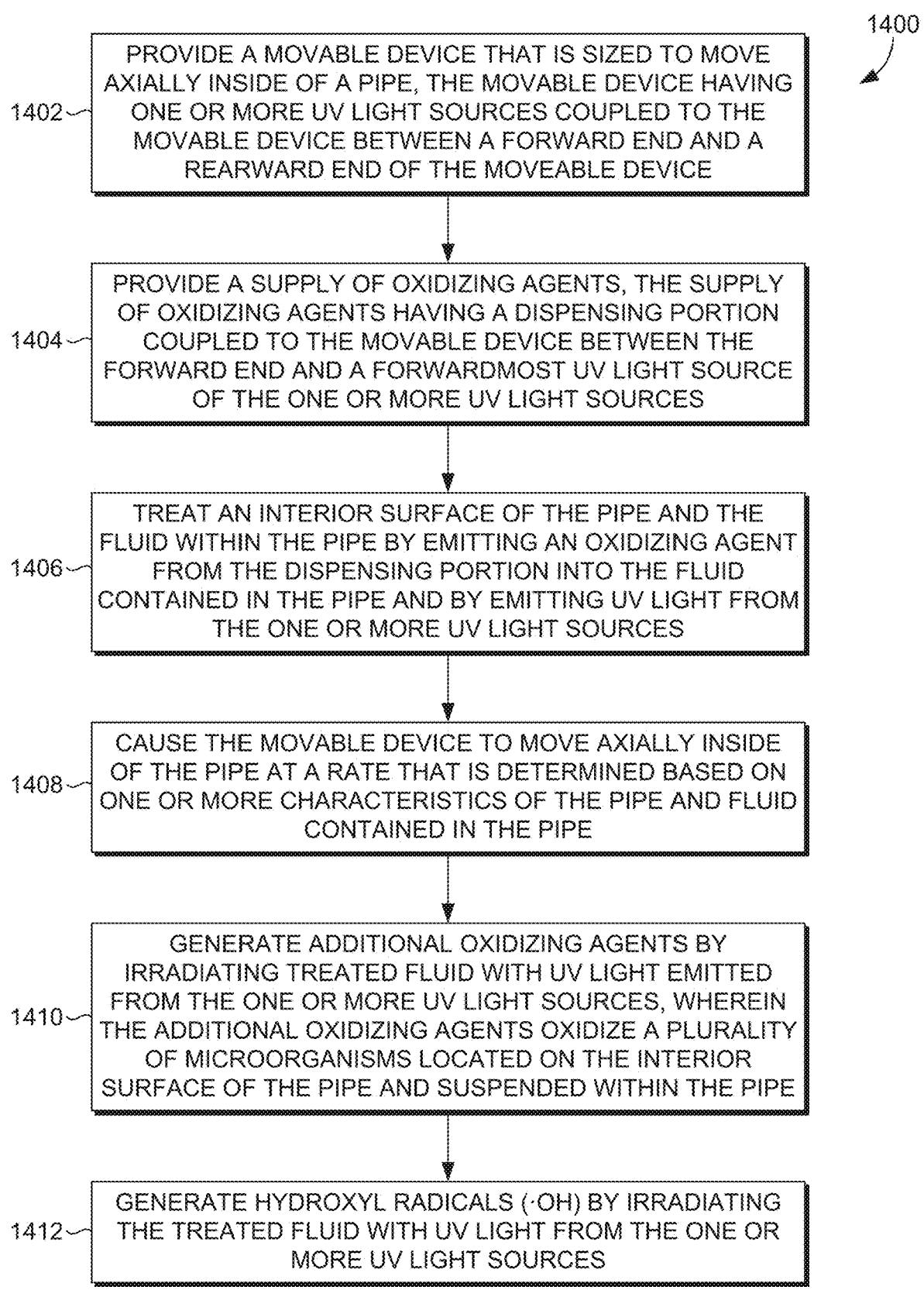
FIG. 14 illustrates a flow diagram of a method of disinfecting water mains.

Turning now to FIG. 14, a flow diagram illustrates a method 1400 for disinfecting water mains. A pipe, such as a water main, is typically disinfected prior to its use in transporting a substance from one location to another within the pipe. For instance, water main pipes transport water from one location to another location. Prior to transporting useable water, the water main is disinfected to kill any bacteria or other harmful organisms on the interior of the pipe or contained within the pipe (e.g., harmful organisms within non-potable or flush water within the pipe).

Initially, a movable device is provided at step 1402. The movable device is sized to move axially inside of the pipe. The movable device has one or more UV light sources coupled to the movable device between a forward end and a rearward end of the movable device. The one or more UV light sources are selected based on various characteristics, including its frequency and intensity. Characteristics of the pipe are taken into consideration when the frequency and intensity of the UV light source are determined. These characteristics may include the material of the pipe and the size (e.g., diameter) of the pipe. For example, a smaller pipe may require a UV light source having a lower frequency and intensity than that required for a larger pipe. The UV light source may provide a pulsed emission of light in one embodiment, but in an alternative embodiment, may provide a continuous emission of light.

At step 1404, a supply of oxidizing agents is provided. The supply of oxidizing agents may have a dispensing portion coupled to the movable device between the forward end and a forwardmost UV light source of the one or more UV light sources.

At step 1406, an interior surface of the pipe and the fluid contained within the pipe is treated by emitting an oxidizing agent from the dispensing portion into the fluid contained within the pipe and by emitting UV light from the one or more UV light sources.

At step 1408, the movable device is caused to move axially inside of the pipe at a rate that is determined based on one or more characteristics of the pipe and the fluid contained within the pipe. These characteristics may include a size and material of a pipe, so that the interior surface of the pipe receives the appropriate dosage of UV light and/or the oxidizing agents as the movable device moves axially in the pipe. As used herein, the dosage of UV light is dictated by the frequency and intensity of the UV light, and the rate of the movable device through the pipe, and refers to quantity of photons emitted from the UV light source. Similarly, the dosage of oxidizing agents is dictated by the mass flow rate of the oxidizing agents. As the one or more UV light sources move in the pipe, the interior surface of the pipe is disinfected, thereby killing harmful pathogenic bacteria or other contaminants. Similarly, as the oxidizing agents are dispensed through the pipe the fluid within the pipe and the interior surface of the pipe is disinfected by the oxidation of harmful pathogenic bacteria or other contaminants.

At step 1410, additional oxidizing agents are generated by irradiating the treated fluid contained within the pipe with the UV light emitted from the one or more UV light sources. The additional oxidizing agents may help supplement oxidation of harmful pathogenic bacteria and therefore increase the efficiency of the disinfection process.

At step 1412, hydroxyl radicals are generated by irradiating the treated fluid with UV light from the one or more UV light sources. As the hydroxyl radicals are generated throughout the pipe, contaminants in the fluid within the pipe are oxidized.

Figure 15:
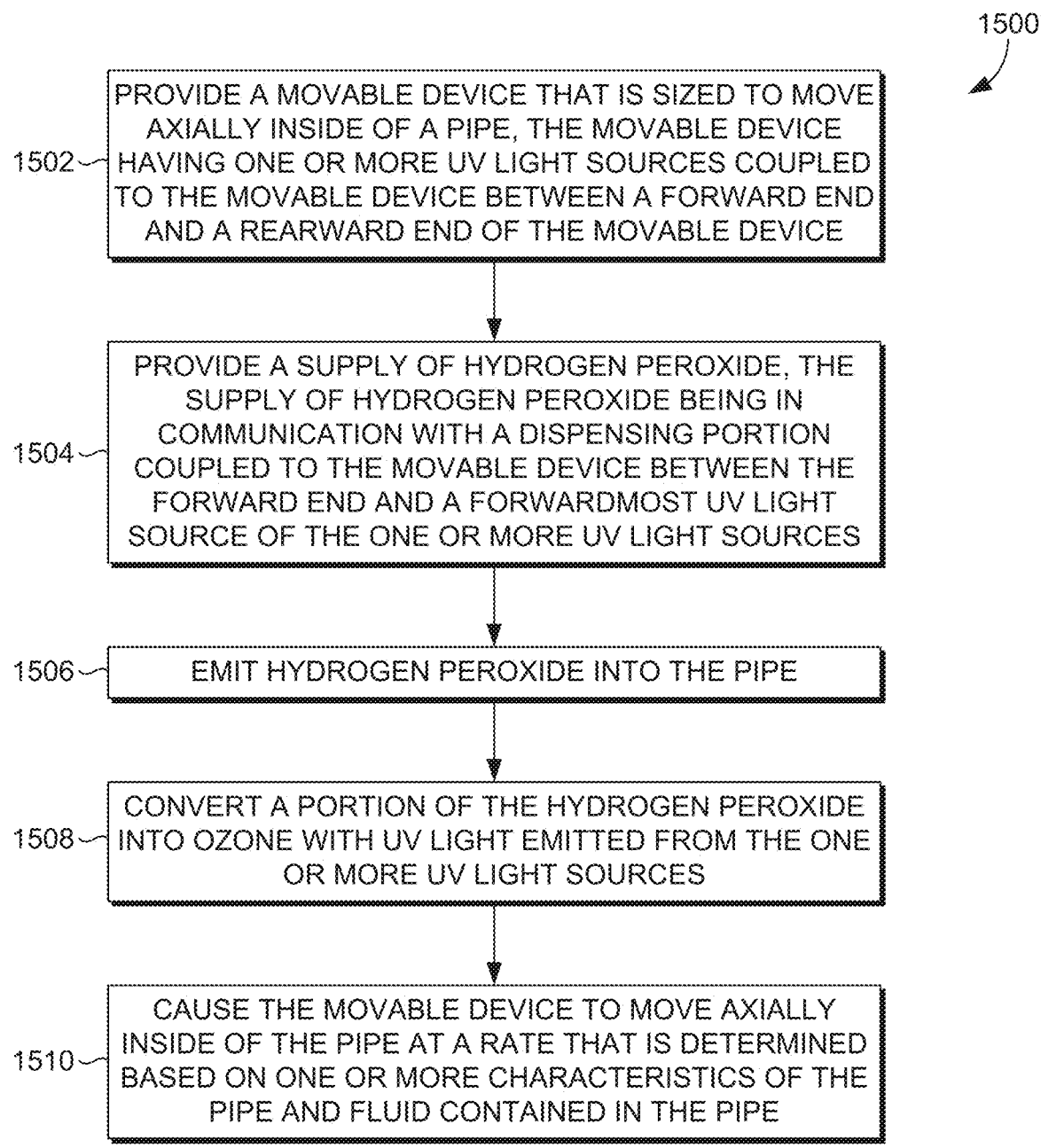
FIG. 15 illustrates a flow diagram of a method of disinfecting water mains.

Turning now to FIG. 15, a flow diagram illustrates a method 1500 for disinfecting water mains. Initially, a movable device is provided at step 1502. The movable device is sized to move axially inside of the pipe. The movable device has one or more UV light sources coupled to the movable device between a forward end and a rearward end of the movable device. At step 1504, a supply of hydrogen peroxide ($H_2O_2$) is provided. The supply of hydrogen peroxide may be in communication with a dispensing portion. The dispensing portion may be coupled to the movable device between the forward end and a forwardmost UV light source of the one or more UV light sources.

At step 1506, hydrogen peroxide may be emitted from the dispensing portion into the pipe. Characteristics of the pipe are taken into consideration when the quantity of the hydrogen peroxide to be emitted is determined. Such characteristics may be the same as those discussed above. At step 1508, a portion of the hydrogen peroxide may be converted into ozone ($O_3$). For example, the emitted UV light may convert a portion of the emitted hydrogen peroxide into ozone. At step 1510, the movable device is caused to move axially inside of the pipe at a rate that is determined based on one or more characteristics of the pipe and the fluid contained within the pipe.

Turning now to FIGS. 16 and 17, some aspects of the above described system 1200 may include a plurality of carriages (such as the remotely-controlled carriage 1206) that operate in cooperation to disinfect the pipe 1202. Each of the plurality of carriages may be configured as described above. For example, the system may include three carriages tethered together in series, which allows the pipe 1202 to receive three doses of UV light and/or oxidizing agents. Any suitable number of carriages may be tethered together in this manner.

In the illustrated aspect, the system 1200 includes three remotely-controlled carriages 1206 coupled together with tether 1262. A pair of winches 1260 pull the tethered remotely-controlled carriages 1206 axially through the pipe 1202. In some aspects, the winches 1260 maintain a tension 1262 in the tether that maintains both the tether 1262 and the remotely-controlled carriages 1206 radially centered within the pipe 1202.

Referring now to FIG. 18, the above described system 1200 may include a pigging component 1264 that is configured to clean the inside surface 1204 of the pipe 1202. The pigging component 1264 may be coupled to a remotely controlled carriage (such as remotely-controlled carriage 1206 described above). The pigging component 1264 may also be an independent component that acts in cooperation with the remotely controlled carriage 1206. When the pigging component 1264 is independent of the remotely controlled carriage 1206, it may be tethered to the remotely controlled carriage 1206 and travel axially through the pipe 1202 in series with the remotely controlled carriage 1206. The pigging component 1264 may be configured to clean bio-films or other deposits 1266 off of the inside surface 1204 of the pipe 1202. The pigging component 1264 may be made from a variety of materials, such as soft foam (e.g., swabs), medium and high density polyurethane foam (e.g., poly pigs), solid polyurethane or metal (e.g., mechanical or mandrel pigs). The pigging component 1264 may be fitted with cups, discs, scrapers, wire brushes, magnets and/or other accessories.

Figure 19:
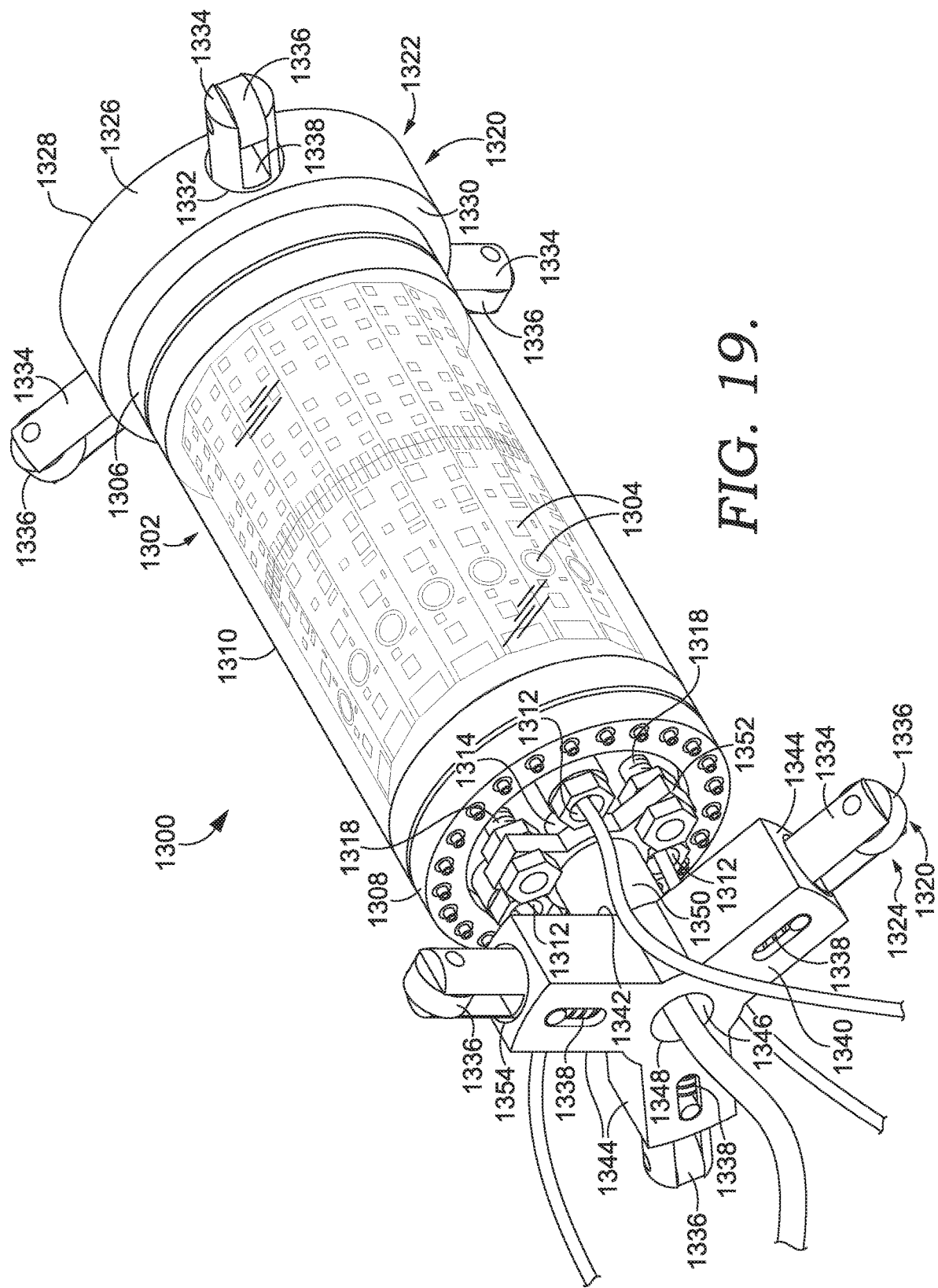
FIG. 19 is a perspective view of a movable device in accordance with an embodiment of the present invention.

Referring now to FIG. 19, another aspect of a movable device 1300 is depicted. The movable device 1300 may include a housing 1302 configured to enclose one or more UV light sources 1304. The housing 1302 may include a first end 1306 opposite a second end 1308, a water-tight wall 1310 the extends from the first end 1306 to the second end 1308 and may be configured to prevent fluid from entering the housing 1302 between the first and second ends. The housing 1302 may also include a mounting structure between the first end 1306 and the second end 1308 configured to mount the one or more UV light sources 1304, peripheral equipment for operating the UV light sources 1304 (e.g., circuit boards, microprocessors, etc.), and peripheral equipment for operating the movable device 1300 (e.g., batteries, wireless receiver, controller, etc.). The water-tight wall 1310 may be made from a material transparent to UV light (e.g., glass) in order to permit UV light emitted from the one or more UV light sources 1304 to pass through the water-tight wall 1310 and contact a structure outside of the housing 1302 (e.g., an interior surface of a pipe).

The first end 1306 and the second end 1308 may each have one or more ports 1312 configured to permit communication from outside of the housing 1302 to an interior portion of the housing 1302. Each of the one or more ports 1312 may be configured to provide a water-tight seal. For example, a tether, conduit, or wire from outside the housing 1302 may couple to the housing 1302 at one of the one or more ports 1312. In some aspects, a central port 1314 may be formed in both the first end 1306 and the second end 1308 and may be in communication with a conduit 1316 that may extend from the first end 1306 and the second end 1308. The conduit 1316 may permit communication through the housing 1302. For example, electrical or mechanical power or a supply of materials (e.g., oxidizing agents) may be provided to a component (e.g., an oxidant supply component, a pig, another housing, etc.) affixed to, or forward of, the first end 1306. In addition, the first end 1306 and the second end 1308 may each include one or more attachment portions 1318 configured to couple the housing 1302 to a movement mechanism 1320.

In some aspects, the movement mechanism 1320 may comprise the remotely-controlled carriage described above. In other aspects, the movement mechanism 1320 may comprise a first portion 1322 and a second portion 1324 respectively coupled to the first end 1306 and the second end 1308 with the one or more attachment portions 1318.

In the illustrated aspect, the first portion 1322 includes cylindrical disc 1326 having a first surface 1328 spaced apart in the axial direction from a second surface 1330 and a plurality of passageways extending through the cylindrical disc 1326 from the first surface 1328 to the second surface 1330. Each passageway receiving one of the one or more attachment portions 1318. The cylindrical disc 1326 also includes a plurality of radial passageways 1332 extending radially outward from an intermediate point of the cylindrical disc 1326 to an aperture formed on a side wall of the cylindrical disc 1326. Each of the radial passageways 1332 configured to slidably receive a bushing 1334. The bushing 1334 has a first end opposite the second end. The second end has a rolling member 1336 coupled proximately thereto. Each of the radial passageways 1332 may also include a spring member 1338 positioned radially interior to the second end of the bushing 1334. The spring member 1338 presses the bushings radially outward in order to hold the rolling member 1336 against an interior surface of a pipe. The first portion 1322 is configured to automatically adjust its effective diameter such that contact between the rolling members 1336 and the interior surface of a plurality of different diameter pipes is maintained. The cylindrical disc 1326 also includes an anchoring member coupled there to. The anchoring may be an eye bolt as depicted or may be another type of connector for anchoring to the first portion 1322 (e.g., for connecting a tether to pull the first portion, the housing and the second portion).

In the illustrated aspect, the second portion 1324 is shaped as depicted and generally includes central portion having a first surface 1340 spaced apart in the axial direction from a second surface 1342 and a plurality of legs 1344 extending radially out from the central portion. The central portion also includes an axial passageway 1346 extending from an aperture 1348 formed on the first surface 1340 to the second surface 1342. The second portion 1324 further includes a tube 1350 in communication with the axial passageway 1346 and extending from the second surface 1342 to a mounting flange 1352 proximate the second end 1308. The mounting flange 1352 couples the second portion 1324 to the second end 1308 and the tube 1350 is configured to be in communication with the central port 1314. Each leg of the plurality of legs 1344 includes a radial passageway 1354 extending radially outward from an intermediate point of the leg to an aperture formed on an end wall of the leg similar to the radial passageway 1332 described above. Each of the radial passageways 1354 is configured to slidably receive a bushing (such as the bushing 1334 described above). Each of the radial passageways 1332 may also include a spring member (such as the spring member 1338 described above) positioned radially interior to an interior end of the received bushing. The spring member presses the received bushing radially outward in order to hold a rolling member (such as the rolling member 1336 described above) associated with the bushing against an interior surface of a pipe. The second portion 1324 is configured to automatically adjust its effective diameter such that contact between the rolling members and the interior surface of a plurality of different diameter pipes is maintained.

In other aspects, each of the first portion 1322 and the second portion 1324 may be interchangeable, such that the movement mechanism 1320 may include two first portions 1322 or two second portions 1324.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure. Further, alternative means of implementing the aforementioned can be completed without departing from the scope of the claims below. Certain features and subcombinations are of utility and may be employed without reference to other features and subcombinations and are contemplated within the scope of the claims.

The invention claimed is:

1. A water-main disinfecting system comprising:
 a remotely-controlled carriage having a receiver, the receiver configured to receive instructions from a remote controller, wherein the remote controller is configured to send signals to the receiver and cause the remotely-controlled carriage to move axially inside of a pipe;
 a UV light source coupled to the remotely-controlled carriage and configured to emit UV light, wherein the emitted UV light irradiates contaminants located on an interior surface of the pipe and suspended within the pipe; and
 an oxidant supply component comprising a storage component configured to store one or more oxidizing agents, and further comprising an oxidizing agent generator configured to produce the one or more oxidizing agents, wherein the oxidizing agent generator is in communication with the storage component; and
 a dispensing component in communication with the storage component, the dispensing component being configured to emit the one or more oxidizing agents and to move axially inside the pipe, wherein the emitted oxidizing agents oxidize the contaminants located on the interior surface of the pipe and suspended within the pipe, and wherein the dispensing component moves axially inside the pipe independently of the remotely-controlled carriage.

2. The water-main disinfecting system of claim 1, wherein the UV light source emits the UV light having wavelengths less than 240 nanometers.

3. The water-main disinfecting system of claim 1, wherein the dispensing component is coupled to the remotely-controlled carriage.

4. The water-main disinfecting system of claim 3, wherein the remotely-controlled carriage has a forward end opposite a rearward end, wherein the dispensing component is coupled to the remotely-controlled carriage nearer to the forward end than is the UV light source such that the oxidizing agents are emitted in the pipe forward of the UV light source.

5. The water-main disinfecting system of claim 1, wherein the storage component is maintained outside of the pipe.

6. The water-main disinfecting system of claim 1, wherein the emitted UV light interacts with at least a portion of the one or more oxidizing agents to generate additional oxidizing agents, wherein the additional oxidizing agents oxidize the contaminants located on the interior surface of the pipe and suspended within the pipe.

7. The water-main disinfecting system of claim 1, wherein the one or more oxidizing agents comprise one or more of oxygen ($O_2$), ozone ($O_3$), or hydrogen peroxide ($H_2O_2$).

8. The water-main disinfecting system of claim 1, wherein the emitted UV light interacts with the one or more oxidizing agents to generate hydroxyl radicals (·OH), wherein the hydroxyl radicals (·OH) oxidize the contaminants suspended within the pipe.

9. The water-main disinfecting system of claim 1, wherein the remotely-controlled carriage comprises:
 a body portion;
 a plurality of pairs of legs, each of the legs of the plurality of pairs of legs having a first end opposite a second end, each of the legs of the plurality of pairs of legs coupled proximate the first end to the body portion and extending towards the interior surface of the pipe; and
 a plurality of contact members, each contact member of the plurality of contact members respectively coupled proximate the second ends of a respective pair of the plurality of pairs of legs and configured to contact the interior surface of the pipe,
 wherein each respective pair of the plurality of pairs of legs is pinned together intermediate the first and second ends.

10. The water-main disinfecting system of claim 9, wherein each of the plurality of contact members comprises a first contact member and a second contact member, wherein each said first contact member is coupled to the second end of one of the respective pair of plurality of pairs of legs and each said second contact member is coupled to the second end of the other of the respective pair of plurality of pairs of legs.

* * * * *